United States Patent [19]
Koketsu et al.

[11] Patent Number: 5,834,423
[45] Date of Patent: Nov. 10, 1998

[54] PHARMACEUTICAL COMPOSITION CONTAINING SIALIC ACID DERIVATIVES

[75] Inventors: Mamoru Koketsu; Masakazu Nishizono; Teruhiko Nitoda; Yuko Enoki; Hiroshi Kawanami; Lekh Raj Juneja, all of Yokkaichi, Japan

[73] Assignee: Taiyo Kagaku Co., Ltd., Mie, Japan

[21] Appl. No.: 617,821

[22] PCT Filed: Jul. 14, 1995

[86] PCT No.: PCT/JP95/01415

§ 371 Date: Mar. 15, 1996

§ 102(e) Date: Mar. 15, 1996

[87] PCT Pub. No.: WO96/02255

PCT Pub. Date: Feb. 1, 1996

[30] Foreign Application Priority Data

Jul. 15, 1994 [JP] Japan .................................. 6-186699
Jul. 15, 1994 [JP] Japan .................................. 6-186700

[51] Int. Cl.$^6$ ........................ A61K 31/70; A61K 31/725; A61K 31/73; A61K 38/02
[52] U.S. Cl. ..................... 514/7; 514/8; 514/22; 514/55; 514/56; 536/2; 536/17.2; 536/123; 536/123.1
[58] Field of Search .............................. 536/2, 17.2, 123, 536/123.1; 514/7, 8, 22, 55, 56

[56] References Cited

FOREIGN PATENT DOCUMENTS

| | | |
|---|---|---|
| 0584558A2 | 3/1994 | European Pat. Off. . |
| WO 86 03971 | 7/1986 | WIPO . |
| WO 92 22301 | 12/1992 | WIPO . |
| WO 93 07291 | 4/1993 | WIPO . |
| WO 93 10134 | 5/1993 | WIPO . |
| WO 95 21618 | 8/1995 | WIPO . |

OTHER PUBLICATIONS

Noriko Takahashi et al., Biochimica et Biophysica Acta, Almond Glycopeptidase Acting on . . . , 657 (1981), pp. 457–467.

Mamoru Koketsu et al., Journal of Carbohydrate Chemistry, An Efficient Preparation and Structural . . . , 14(6), pp. 833–841 (1995).

Mamoru Koketsu et al., Journal of Agricultural and Food Chemistry, Sialyloligosaccharides from Egg Yolk . . . , 1995, 43, No. 4, pp. 858–861.

Mamoru Koketsu et al., Journal of Food Science, Sialyloligosaccharides of Delipidated Egg Yolk . . . , 58(4), pp. 743–747 (1993).

Hasegawa et al., *Jpn. J. Med. Sci. Biol.*, vol. 47, pp. 73–85 (1994).

Endo et al., *Biochemistry*, vol. 28, pp. 8380–8388 (1989).

Spik et al., *Biochimie*, vol. 70, pp. 1459–1469 (1988).

Schmid et al., *Biorganic & Medicinal Chemistry Letters*, vol. 3, No. 4, pp. 747–752 (1993).

Mochalova et al., *Antiviral Research*, vol. 23, pp. 179–190 (1994).

Pegg et al., *Biochemistry and Molecular Biology International*, vol. 32, No. 5, pp. 851–858 (Apr. 1994).

Ebina et al., *Microbiol. Immunol.*, vol. 34, No. 7, pp. 617–629 (1990).

*Primary Examiner*—John Kight
*Assistant Examiner*—D. Margaret M. Mach
*Attorney, Agent, or Firm*—Birch, Stewart, Kolasch & Birch, LLP

[57] ABSTRACT

The present invention is a pharmaceutical composition used as an antiviral agent, a diarrheal remedy, an antiulcer agent, an anti-inflammatory agent, an anti-allergic agent and an agent for promoting the proliferation of Bifidobacteria, characterized by containing a sialic acid derivative as an active ingredient. The method for producing a sialic acid derivative of the present invention is characterized in that an almond or apricot seed is added to an avian egg yolk, by which the desired product can easily be obtained in a high yield.

27 Claims, 3 Drawing Sheets

PHARMACEUTICAL COMPOSITION CONTAINING SIALIC ACID DERIVATIVES

This application is a 371 of PCT/JP95/01415, filed Jul. 14, 1995.

TECHNICAL FIELD

The present invention relates to a pharmaceutical composition containing sialic acid derivatives and methods for producing sialic acid derivatives from avian egg yolk.

BACKGROUND ART

Much effort has been made to develop therapeutic/prophylactic agents for viral diseases, but thus far no effective antiviral agents against certain viruses have been developed. Influenza, caused by influenza virus, in particular, threatens people all over the world, because it becomes prevalent on a global scale once in several years, resulting in a large number of victims. However, it is very difficult to develop an effective drug against influenza virus, because its antigen shows high variability.

Rotavirus, a virus that causes severe diarrheal diseases in humans and other animals, is highly infectious to infants during the lactation period, causing many deaths owing to low levels of medical technology and equipment in developing countries. It also causes vast damage to the livestock industry. Nevertheless, there have been no effective prophylactic/therapeutic methods for diseases associated with rotavirus.

Herpesvirus causes diseases of various symptoms, including chronic herpes, in humans and other animals, but there have been no well-established radical methods for preventing or treating such diseases, partially due to latent infection.

Newcastle disease virus causes Newcastle disease, a fatal infectious disease of birds, causing significant damage to a large number of poultry farms. Although some prophylactic measures by vaccination have been taken, complete prophylaxis cannot be achieved. In addition, Newcastle disease is rapidly communicable and gives a constant threat of infection with foreign viruses in the poultry industry.

Diarrheal diseases can be roughly divided into two types: Infectious diarrhea caused by viruses, bacteria, etc., and non-infectious diarrhea caused by stress etc. However, it is difficult to determine the cause of each diarrheal disease. Infectious diarrhea in human infants is thought to be caused mainly by rotavirus, and rotaviral diarrhea is said to cause more than one million infantile deaths in developing countries every year. As stated above, however, there are diarrheal diseases caused by other viruses, or by bacteria or stress, and the onset of most diarrheal diseases involves complex association with such multiple causes. Therefore, in order to effectively prevent or treat diarrhea, a means that exerts its effect on the multiple causes are needed. In livestock and poultry as well, diarrheal diseases during the nursing period account for high morbidity and high lethality, and have caused great damage to the livestock and poultry industries. Most of these diarrheal diseases appear to be caused by multiple causes. However, no prophylactic/therapeutic methods are effective for diarrheal diseases caused by multiple factors.

Sialyloligosaccharides occur naturally as oligosaccharide chains in glycoprotein molecules, oligosaccharide chains in gangliosides, and oligosaccharide peptides or oligosaccharide chains released from glycoproteins or gangliosides.

As sialyloligosaccharides found in avian egg yolk, those bound to the phosvitin molecule are known [Shainkin, R., and Perlmann, G. E. (1971), Arch. Biochem. Biophys. 145, 693–700].

In recent years, many studies have elucidated the biological significance of sialyloligosaccharides. Sialyloligosaccharides bound to glycoproteins are involved in various aspects of protein molecules, including the retention of tertiary structure, increased resistance to proteases, half-life in blood, intermolecular interaction, and increased solubility. They also affect intercellular recognition, cell differentiation, etc. as an important component of gangliosides, playing roles as a receptor for various cytotoxins, neurotransmitters, hormones, interferons, viruses, etc. Sialyloligosaccharides play a significant role in the initial stage of inflammation (sialyl Lewis-X antigen involvement), ulcer caused by *Helicobacter pylori* and influenza virus infection. With regards to biological functions of sialic acid derivatives concerning influenza virus, hemagglutination and antitussive effects (Japanese Patent Laid-Open No. 61/68418), and the use as an anti-infectious agent (Japanese Patent Laid-Open No. 63/284133) are disclosed.

It is known that human breast milk contains sialic acid at a concentration of 1.5 to 7.0 times that in cow's milk, and various effects have been suggested, which include increasing immunity in infants, development of cerebral function, and promotion of useful enteric bacterial proliferation. On the basis of these findings, research has been undertaken to apply sialyloligosaccharides to pharmaceuticals and functional foods.

A method for purifying sialyloligosaccharides from delipidated avian egg yolk on an industrial scale is known. This method is characterized in that delipidated avian egg yolk, as it is or in the form of aqueous extract, is enzymatically digested and processed using an ultrafiltration or reverse osmosis membrane (Japanese Patent Laid-Open No. 6/245784). Enzymes used in the above method include proteases and PNGase (peptide-N-glycanaze); the former acts to release glycopeptides from glycoproteins, and the latter acts to release N-glycoside type sugar chains from glycoproteins or glycopeptides. However, the sialyloligosaccharide peptides or sialyloligosaccharides obtained using these enzymes are mixtures of the monosialyl and disialyl types. In addition, sialyloligosaccharide peptides can be immunogenic, because they have a peptide consisting of 5 or 6 amino acids at the reduction end thereof. Moreover, most kinds of PNGase are derived from pathogenic bacteria. For this reason, the application of such enzymes to foods has been difficult. The PNGase is found in almond seeds, but enzymes such as proteases, β-D-galactosidase, β-D-glucosidase, and α-D-mannosidase are also present in almond seeds, thereby making it difficult to purify PNGase on a large scale. Moreover, the applicability of PNGase has been limited, because it is incapable of releasing sugar chains bound to giant densely folded protein molecules, such as phosvitin.

DISCLOSURE OF INVENTION

Accordingly, an object of the present invention is to provide a pharmaceutical composition containing a sialic acid derivative as an active ingredient. Another object of the present invention is to provide a method for inexpensively and conveniently producing a sialic acid derivative on an industrial scale.

Through extensive investigation, the present inventors found that a sialic acid derivative of particular structure unexpectedly shows excellent antiviral effect, antidiarrheal effect, antiulcer effect, anti-inflammatory effect and antiallergic effect, and possesses an excellent activity of promoting proliferation of Bifidobacteria, an enteric bacterium.

The inventors also found that, when avian egg yolk is used as a substrate, a sialyloligosaccharide chain can be released very easily, resulting in easy and efficient obtainment of the desired product, solely by adding an almond or apricot seed as it is, rather than purified PNGase. The inventors made further investigation based on these findings, and developed the present invention.

The following is the gist of the present invention:

(a) A pharmaceutical composition characterized by containing as an active ingredient a sialic acid derivative represented by the general formula (1) or (2) below:

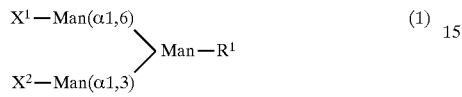
(1)

wherein $R^1$ represents a sugar residue or a glycopeptide residue; and $X^1$ and $X^2$, which may be identical or different, represent NeuAc($\alpha$2,6)Gal($\beta$1,4)GlcNAc($\beta$1,2)-, Gal($\beta$1,4)GlcNAc($\beta$1,2)- or GlcNAc($\beta$1,2)-, provided that at least one of $X^1$ and $X^2$ represents NeuAc($\alpha$2,6)Gal($\beta$1,4)Glc NAc($\beta$1,2)-,

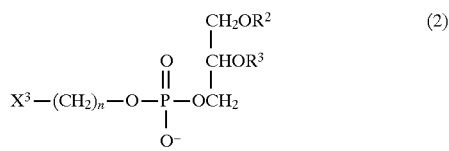
(2)

wherein $R^2$ and $R^3$, which may be identical or different, represent a hydrogen atom or a linear, branched or cyclic, saturated or unsaturated acyl group having 1 to 30 carbon atoms; n is an integer of 1 to 20; and $X^3$ represents a sialic acid derivative residue or a sialyloligosaccharide derivative residue represented by the general formula (3) below:

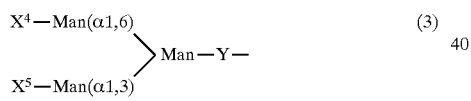
(3)

wherein $X^4$ and $X^5$, which may be identical or different, represent NeuAc($\alpha$2,6)Gal($\beta$1,4)GlcNAc($\beta$1,2)-, Gal($\beta$1,4)GlcNAc($\beta$1,2)- or GlcNAc($\beta$1,2)-, provided that at least one of $X^4$ and $X^5$ represents NeuAc($\alpha$2,6)Gal($\beta$1,4)Glc NAc($\beta$1,2)-; and Y represents a sugar residue;

(b) The pharmaceutical composition described in (a) above which is used as an antiviral agent;

(c) The pharmaceutical composition described in (a) above which is used as a remedy for diarrhea;

(d) The pharmaceutical composition described in (a) above which is used as an antiulcer agent;

(e) The pharmaceutical composition described in (a) above which is used as an anti-inflammatory agent;

(f) The pharmaceutical composition described in (a) above which is used as an anti-allergic agent;

(g) The pharmaceutical composition described in (a) above which is used as a promoting agent for Bifidobacteria proliferation;

(h) A method for producing a sialic acid derivative represented by the following general formula (4) characterized in that an almond is added to an avian egg yolk:

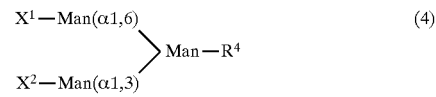
(4)

wherein $R^4$ represents a sugar residue; $X^1$ and $X^2$, which may be identical or different, represent NeuAc($\alpha$2,6)Gal($\beta$1,4)GlcNAc($\beta$1,2)-, Gal($\beta$1,4)GlcNAc($\beta$1,2)- or GlcNAc($\beta$1,2)-, provided that at least one of $X^1$ and $X^2$ represents NeuAc($\alpha$2,6)Gal($\beta$1,4)GlcNAc($\beta$1,2)-;

(i) The method described in (h) above, wherein the almond is delipidated;

(j) A method for producing a sialic acid derivative represented by the following general formula (4) characterized in that an apricot seed is added to an avian egg yolk:

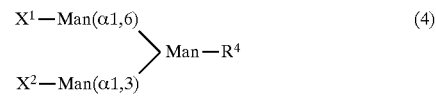
(4)

wherein $R^4$ represents a sugar residue; $X^1$ and $X^2$, which may be identical or different, represent NeuAc($\alpha$2,6)Gal($\beta$1,4)GlcNAc($\beta$1,2)-, Gal($\beta$1,4)GlcNAc($\beta$1,2)- or GlcNAc($\beta$1,2)-, provided that at least one of $X^1$ and $X^2$ represents NeuAc($\alpha$2,6)Gal($\beta$1,4)GlcNAc($\beta$1,2)-; and (k) The method described in (j) above, wherein the apricot seed is delipidated.

BEST MODE FOR CARRYING OUT THE INVENTION

Figure 1:
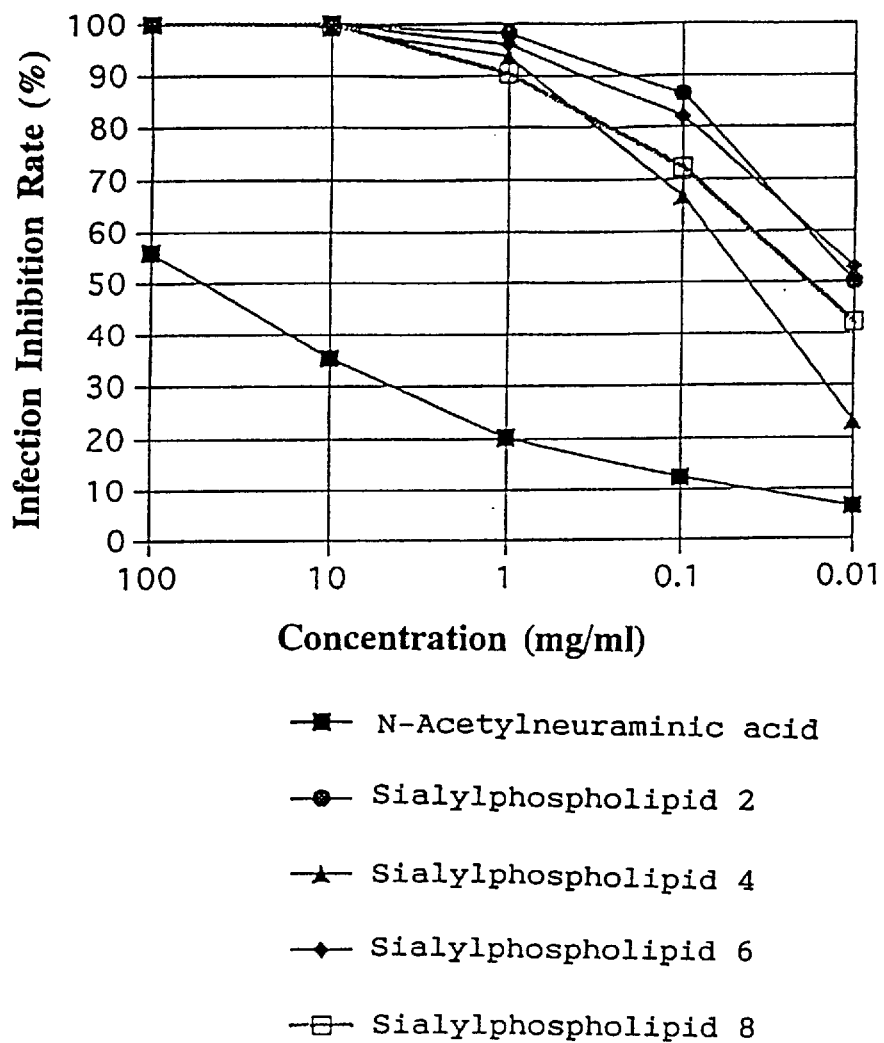
FIG. 1 shows an inhibition of human rotaviral infection by a sialic acid derivative (sialylphospholipid).

The pharmaceutical composition of the present invention contains as an active ingredient a sialic acid derivative represented by the general formula (1) or (2) below.

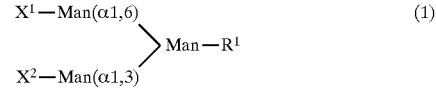
(1)

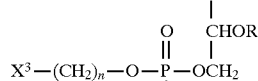
(2)

Compounds represented by the general formula (1)

In the general formula (1), $R^1$ represents a sugar residue or a glycopeptide residue. Such sugar residues include, but are not limited to, -GlcNAc($\beta$1,4)GlcNAc, -GlcNAc and -Gal($\beta$1,4)Glc. Such glycopeptides include, but are not limited to, -GlcNAc($\beta$1,4)GlcNAcAsn, -GlcNAcAsn, IleLysValAlaAsp(-GlcNAc)LysThr and LysValAlaAsp(-GlcNAc)LysThr.

$X^1$ and $X^2$, which may be identical or different, represent NeuAc($\alpha$2,6)Gal($\beta$1,4)GlcNAc($\beta$1,2)-, Gal($\beta$1,4)GlcNAc($\beta$1,2)- or GlcNAc($\beta$1,2)-. At least one of $X^1$ and $X^2$ represents NeuAc($\alpha$2,6)Gal($\beta$1,4)GlcNAc($\beta$1,2)-.

Compounds represented by the general formula (2)

In the general formula (2), $R^2$ and $R^3$, which may be identical or different, represent a hydrogen atom or a linear, branched or cyclic saturated or unsaturated acyl group having 1 to 30 carbon atoms, preferably 12 to 24 carbon atoms. The linear, branched or cyclic saturated or unsaturated acyl groups having 1 to 30 carbon atoms include, but are not limited to, lauroyl, myristoyl, palmitoyl, stearoyl, oleoyl, linoleoyl, linolenoyl, arachidonoyl, eicosapentaenoyl and docosahexaenoyl groups, with a preference given to lauroyl, myristoyl, palmitoyl and stearoyl groups because of high availability.

In the present specification, $-(CH_2)n-$ in the general formula (2) is referred to as a spacer. The numeral n in the spacer represents an integer from 1 to 20, preferably 4 to 16, more preferably 6 to 12, and most preferably 8 to 10. It is preferable that n be 1 or more, from the viewpoint of prevention of membrane impregnation of the sialic acid derivative residue or sialyloligosaccharide derivative residue represented by $X^3$, and that n be 20 or less, from the viewpoint of flexibility.

$X^3$ represents a sialic acid derivative residue or a sialyloligosaccharide derivative residue represented by the general formula (3) below:

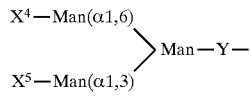

(3)

wherein $X^4$ and X5, which may be identical or different, represent NeuAc(α2,6)Gal(β1,4)GlcNAc(β1,2)-, Gal(β1,4)GlcNAc(β1,2)-, or GlcNAc(β1,2)-, provided that at least one of $X^4$ and $X^5$ represents NeuAc(α2,6)Gal(β1,4)GlcNAc(β1,2)-; and Y represents a sugar residue.

The sialic acid derivative residue mentioned herein is not subject to limitation, but is exemplified by those derived from the following compounds:

3'-sialyllactose, 6'-sialyllactose, sialyl Lewis X, N-acetylneuraminic acid, O-acetylneuraminic acid, N-glycolylneuraminic acid, O-glycolylneuraminic acid and 3-deoxynonulosic acid, and alkyl esters, O-acylates, O-alkylates, deoxies, thioglycosides and lactones thereof. Of these compounds, 3'-sialyllactose, 6'-sialyllactose and N-acetylneuraminic acid, and alkyl esters, O-acylates, O-alkylates and deoxies thereof are preferred, with a greater preference given to N-acetylneuraminic acid.

In the general formula (3), Y represents a sugar residue. Such sugar residues include, but are not limited to, -GlcNAc(β1,4)GlcNAc-, -GlcNAc- and -Gal(β1,4)Glc-.

Accordingly, the sialyloligosaccharide derivative residue represented by the general formula (3) is exemplified by the following:

-continued

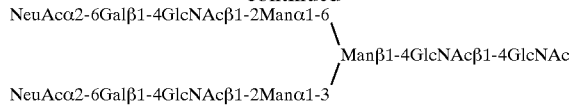

Methods for producing sialic acid derivatives represented by the general formula (1) or (2) are described below.

A sialic acid derivative represented by the general formula (1) can, for example, be obtained by digesting a glycoprotein having a sugar chain structure of the general formula (1) with pronase or PNGase by a conventional method, or by the method of the present invention, which uses avian egg yolk.

The method of the present invention for producing a sialic acid derivative using avian egg yolk is hereinafter described in more detail.

Although the avian egg yolk used for the present invention is not subject to limitation as to its origin, as long as it is the yolk of an avian egg, a preference is given to the yolks of poultry including hens, quails, ducks, and wild ducks. When used as a starting material, the yolk may be in a liquid or a powder form. The residue (delipidated yolk) resulting from delipidation of avian egg yolk by organic solvent extraction (e.g., methanol, ethanol, diethyl ether) may be used as a starting material.

The almond and apricot seeds used for the present invention are not subject to limitation, as long as they are used without being treated for enzyme purification, or as long as the treatment, if any, does not involve heating and any other procedures which inactivate the enzyme contained therein. They may be in the form of powder, paste, or the like. In the present invention, delipidated almond seeds and delipidated apricot seeds are preferred. Delipidated almond seeds and delipidated apricot seeds are not processed into purified enzymes, but are obtained by, for example, defatting raw almond and raw apricot seeds by organic solvent extraction (e.g., acetone and diethyl ether). Defattery treatment should decrease the lipid content to not more than 25%, more preferably not more than 5%. In the present invention, powders, pastes, etc., of such delipidated almond seeds or delipidated apricot seeds are more preferably used. It should be noted that the use of a purified enzyme as in conventional methods yields a mixture of nearly equal proportion of the monosialyl and disialyl types, while the present invention unexpectedly yields a mixture of a very small amount of the monosialyl type and a large amount of the disialyl type, thus offering a great advantage of easy separation between the two types.

An example procedure for the above-described production method of the present invention using avian egg yolk and almond, etc. is described below.

To delipidated avian egg yolk, water or a brine (a solution of a potassium salt, a sodium salt or a salt capable of buffering over the range of pH 5 to 10) is added, followed by stirring at 4° to 80° C., preferably 4° to 40° C., for 10 minutes to 3 days, after which the mixture is filtered to separate the insoluble protein. To the extraction filtrate thus obtained, 0.5 to 20 g of delipidated almond powder or delipidated apricot seed powder per liter of the filtrate is added, followed by stirring at pH 5.0 to 5.5 and 30° to 45° C. for 8 to 24 hours. After filtration, this solution is adsorbed to an anion exchange resin; after washing with water, gradient elution is conducted using 0 to 0.3 M NaCl solution. The eluate thus obtained is desalinized and concentrated using a reverse osmosis membrane (RO membrane), after which it is lyophilized to yield a sialic acid derivative.

The anion exchange resin used here is exemplified by DOWEX (produced by Dow Chemical), SEPABEADS (produced by Mitsubishi Chemical) and AMBERLITE (produced by Rohm & Haas). Although these products are not subject to limitation as to type, those of strongly alkaline type are preferred.

The sialic acid derivative thus obtained is represented by the general formula (4), and is identical with that represented by the general formula (1), except that $R^4$ is not a glycopeptide residue but a sugar residue.

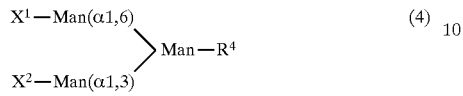

wherein $R^4$ represents a sugar residue; $X^1$ and $X^2$, which may be identical or different, represent NeuAc($\alpha$2,6)Gal($\beta$1,4)GlcNAc($\beta$1,2)-, Gal($\beta$1,4)GlcNAc($\beta$1,2)- or GlcNAc($\beta$1,2)-. At least one of $X^1$ and $X^2$ represents NeuAc($\alpha$2,6)Gal($\beta$1,4)GlcNAc($\beta$1,2)-.

This production method is industrially very advantageous, because it enables less expensive and more convenient production of a sialic acid derivative represented by the general formula (4) than by conventional methods, and because the sialic acid derivative obtained can be used for the pharmaceutical composition of the present invention and the starting materials therefor.

The method for producing a sialic acid derivative represented by the general formula (2) is described below. The sialic acid derivative can be prepared by combining a chemical synthesis reaction and an enzymatic synthesis reaction employing phospholipase D (hereinafter referred to as PLD) using a sugar component, a phospholipid and a spacer material compound as starting materials.

The sugar component mentioned here is a compound having in its structure one of the sialic acid derivative residues or sialyloligosaccharide derivative residues listed above and represented by $X^3$.

The phospholipid may be any phospholipids, as long as it has a hydrogen atom or the acyl group described above, i.e., the acyl group mentioned in the above description of $R^2$ and $R^3$. Specifically, such phospholipids include phosphatidylcholine, phosphatidylserine, phosphatidylethanolamine, phosphatidylinositol and phosphatidylglycerol, all having the acyl group described above. These phospholipids may be used singly, or in combination of two or more kinds. With regards to the origin, the phospholipid may be derived from a plant, such as soybean, or from an animal, such as a hen egg. The phospholipid may also be chemically or enzymatically synthesized from these sources.

The preferred spacer materials are alkyldiols having 1 to 20 carbon atoms. Such alkyldiols include 1,2-ethanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol and 1,12-dodecanediol.

The PLD used for the present invention may be derived from an animal, a plant or a microorganism. Examples of microbial PLD include those derived from the genera Streptomyces, Nocardiopsis and Actinomadura. PLD is used in an aqueous solution or an appropriate buffer solution, or as immobilized to a carrier. Examples of buffers include acetate buffer, phosphate buffer and Tris-hydrochloric acid buffer. Examples of carrier resins include octyl-Sepharose (produced by Pharmacia) and butyl-Toyopearl (produced by Tosoh). Bacterial cells having PLD can also be used. In this case, intact cells are used in the form of dry product, or as immobilized to a carrier.

Specific procedures for preparation of a sialic acid derivative represented by the general formula (2) are described below.

In the first method, a sugar component bound with a spacer is exchanged with the polar group moiety of a phospholipid by transphosphatidylation using PLD.

First, the sugar component is methylated by the action of methanol under acidic conditions; the resulting methylated product is treated with hydrogen chloride in acetyl chloride to acetylate all hydroxyl groups and yield a peracetyl-2-chloro derivative wherein the 2-position hydrogen atom of the sugar residue at the reducing end of the sugar component has been replaced with a chlorine atom. It is then treated with a monoester of an alkyldiol in the presence of a molecular sieve and $Ag_2CO_3$ to yield a peracetyl-2-O-alkyl derivative. This alkyl derivative is deacetylated under alkaline conditions to yield an O-alkylate of the sugar component. This alkylate is dissolved in a buffer of appropriate pH (4.0 to 8.0), followed by the addition of a calcium salt. To this solution, PLD or PLD-containing bacterial cells are added, and a phospholipid, previously dissolved in an organic solvent, is added, and an enzyme reaction is carried out for several hours while the mixture is stirred.

A product resulting from transphosphatidylation between the polar group moiety of the phospholipid and the O-alkylate of the sugar component is obtained, which is then demethylated by the treatment with an alkali metal hydroxide, after which it is purified to yield the desired sialic acid derivative.

The conditions for the enzyme reaction using PLD in this method are, for example, as follows: pH of the reaction mixture is normally 4.0 to 8.0, preferably 5.6 to 7.0. It is preferable that the reaction mixture be adjusted to a pH level in the range of ±0.5 from the optimum pH of the PLD used. If pH falls out of this range, the reaction rate decreases. Also, the amount of PLD used is normally 10 to 100 units, preferably 20 to 50 units, per gram of phospholipid. The amount of PLD added is preferably not less than 10 units from the viewpoint of satisfactory progress of the reaction, and not more than 100 units from the viewpoint of reaction efficiency. Reaction temperature is normally 15° to 50° C., preferably 25° to 30° C. Reaction time is normally 0.5 to 12 hours, preferably 1 to 6 hours, and preferably not shorter than 0.5 hours from the viewpoint of satisfactory progress of the reaction and not longer than 12 hours from the viewpoint of reaction efficiency and prevention of side reactions.

In addition, to further improve the enzyme activity of PLD, it is more preferable to add a calcium salt, but salts of other ions may be added. Such salts include halides, carbonates, phosphates and acetates of divalent typical element ions, such as calcium ion and barium ion, and those of transition element ions, such as manganese, lanthanum and cerium. The amount of the salt added is normally 10 mM to 1 M, preferably 10 mM to 0.5 M, based on the amount of the reaction mixture. The amount is preferably not less than 10 mM from the viewpoint of obtainment of the desired effect and not more than 1 M from the viewpoint of reaction efficiency.

Although the reaction system may be an aqueous system, a biphasic system of water and organic solvent, or an organic solvent system, a preference is given to a biphasic system of water and organic solvent, because most sugar components are soluble in water while phospholipids are soluble in organic solvent.

Organic solvents which are used to dissolve phospholipids include one or more kinds selected from the group consisting of alkyl esters and alkyl ethers of carboxylic acids, aliphatic hydrocarbons, alicyclic hydrocarbons, aromatic hydrocarbons and halogenated hydrocarbons, each having a melting point of 40° C. or lower.

Examples of alkyl esters of carboxylic acids include esters formed between linear or branched fatty acids having 2 to 6 carbon atoms and linear or branched alcohols having not more than 8 carbon atoms, and are exemplified by methyl acetate, ethyl acetate, methyl valerate, methyl propionate, methyl butyrate and methyl caproate, with a preference given to methyl acetate. Alkyl ethers include linear or branched alkyl ethers having 2 to 6 carbon atoms, and are exemplified by dimethyl ether, diethyl ether, ethyl methyl ether and isopropyl ether, with a preference given to diethyl ether. Aliphatic hydrocarbons include linear or branched aliphatic hydrocarbons having 6 to 12 carbon atoms, with a preference given to hexane, heptane and petroleum ether. Alicyclic hydrocarbons include alicyclic hydrocarbons having 6 to 12 carbon atoms with or without a substituent, with a preference given to cyclohexane, methylcyclohexane and cyclooctane. Aromatic hydrocarbons include aromatic hydrocarbons having 6 to 12 carbon atoms with or without a substituent, with a preference given to benzene, toluene and xylene. Halogenated hydrocarbons include chlorides, bromides and iodides of linear or branched alkanes having 8 or fewer carbon atoms, with a preference given to chlorine compounds, such as chloroform, carbon tetrachloride and methylene chloride.

The alkali metal hydroxide used in the demethylating reaction is exemplified by sodium hydroxide and potassium hydroxide. The demethylating reaction is normally carried out under ice-cooling conditions, the reaction time being about 30 minutes to 1 day. By subjecting the reaction product to an ordinary purification method, such as extraction, chromatography or recrystallization, the desired sialic acid derivative can be obtained.

In the second method, a spacer is bound to a phospholipid by transphosphatidylation with PLD, followed by glycosyl binding to a sugar component.

Specifically, the phospholipid and an alkyldiol are mixed in an organic solvent; to this mixture, a buffer of appropriate pH is added to dissolve the calcium salt. To this solution, PLD or PLD-containing bacterial cells are added, followed by an enzyme reaction for several hours while the solution is stirred. An intermediate resulting from transphosphatidylation between the polar group moiety of the phospholipid and the alkyldiol is thus obtained. This intermediate, and the benzyl ester of the peracetyl-2-chloro derivative of the sugar component, synthesized by the method described above, are glycosylated in the presence of an activator at a low temperature of under 0° C. to yield an acetylated product of the desired sialic acid derivative. This acetylated product is then deacetylated by treatment with an alkali metal hydroxide, followed by debenzylation by hydrogenation in the presence of a catalyst to yield the desired sialic acid derivative.

The activator used in the glycosylating reaction is exemplified by trimethylsilyl triflate and silver triflate, with a preference given to silver triflate. The amount of activator added is normally 0.1 to 10 equivalents, preferably 0.1 to 5 equivalents. The amount is preferably not less than 0.1 equivalent from the viewpoint of satisfactory progress of the reaction and not more than 10 equivalents from the viewpoint of reaction efficiency.

The sugar chain structure of the sialic acid derivative used for the present invention can be identified by a known method using HPLC or NMR.

The sialic acid derivative thus obtained can be prepared as a liquid, tablet, granule or other dosage forms using appropriate solvents or base materials to yield the pharmaceutical composition of the present invention.

The pharmaceutical composition of the present invention is preferably used as an antiviral agent, diarrhea remedy, antiulcer agent, anti-inflammatory agent, anti-allergic agent and promoter for Bifidobacteria proliferation. When used as an antiviral agent, the pharmaceutical composition of the present invention is not subject to limitation as to target virus, but it is preferably used for influenza virus, rotavirus, Newcastle disease virus, herpesvirus, etc. When used as a diarrhea remedy, the pharmaceutical composition of the present invention is preferably used for both non-infectious diarrheal diseases, and infectious diarrheal diseases, such as those caused by rotavirus or Salmonella. When used as an antiulcer agent, the pharmaceutical composition of the present invention is preferably used for ulcers caused by *Helicobacter pylori*. When used as an anti-inflammatory agent, the pharmaceutical composition of the present invention is preferably used for rheumatism, asthma, etc. When used as an anti-allergic agent, the pharmaceutical composition of the present invention is preferably used for allergic rhinitis, pollenosis, etc.

With regards to the pharmaceutical composition of the present invention, sialic acid derivative components represented by the general formula (1) or (2) may be used singly, or as a mixture of two or more components.

The dose of the pharmaceutical composition of the present invention varies depending on patient age, sex, body weight, symptoms, and other factors, but, for use as an antiviral agent, the dose is 1.0 to 300 $\mu$g per kg body weight. For use as a diarrhea remedy, the dose is 0.5 to 10 mg per kg body weight. For use as an antiulcer agent, the dose is 1.0 to 2000 $\mu$g per kg body weight. For use as an anti-inflammatory agent, the dose is 1.0 to 100 $\mu$g per kg body weight. For use as an anti-allergic agent, the dose is 1.0 to 300 $\mu$g per kg body weight. For use as a promoter for Bifidobacteria proliferation, the dose is 100 to 1000 m g per kg body weight.

The present invention is hereinafter described in more detail by means of the following production examples, working examples and test examples, but these examples are not to be construed as limitative.

Production Example 1

Preparation of N-Acetylneuraminylphospholipid

Three grams of N-acetylneuraminic acid was dissolved in 300 ml of methanol. Three grams of "Dowex-50"($H^+$ form) (manufactured by Dow Chemical) was added to the above mixture, and the obtained mixture was then stirred at room temperature for 4 hours. After completion of the reaction, the reaction mixture was filtered to remove the "Dowex-50." The filtrate methanol solution was concentrated to a volume of 15 ml and cooled to –20° C. To this concentrate, 6 ml of diethyl ether was added at the above temperature, to yield 2.47 g of a methylated product of N-acetylneuraminic acid by recrystallization.

To the methylated product thus obtained, 25 g of acetyl chloride and 3 g of acetic acid anhydride were added at –20° C. Subsequently, the reaction vessel was saturated with dry gaseous hydrogen chloride, and the obtained mixture was stirred at room temperature for 20 hours. After the solvent was distilled off, the reaction mixture was completely dehydrated with benzene and toluene. This product was then recrystallized from a mixture comprising the equal amounts of dichloromethane, diethyl ether, and hexane to yield 3 g of an acetylated product.

This acetylated product was dissolved in 60 ml of dichloromethane containing 6 g of Molecular Sieve 4A, 5 g of $Ag_2CO_3$ and 3 g of 1,8-octanediol monomethyl ester, at –20° C., and the obtained mixture was stirred at room temperature for 3 hours, to carry out a glycosylation reaction. After the reaction mixture was filtered through Celite, the solvent was distilled off. The residue was then purified by silica gel column chromatography ($CH_2Cl_2$:MeOH= 98:2) to yield 1.9 g of a glycosylated product (Rf=0.63 silica gel/$CH_2Cl_2$:MeOH=15:1).

Under ice-cooling conditions, 1.9 g of the glycosylated product was dissolved in 30 ml of completely dehydrated methanol. Under ice-cooling conditions, 300 mg of potassium was added to the completely dehydrated methanol to produce potassium methoxide, which was then added to a methanol solution of the previously prepared glycosylated product. After the reaction was carried out while the mixture was stirred at 0° C. for 3 hours, Dowex-50 ($H^+$ form) was added to the reaction mixture at −20° C. After the reaction mixture was filtered to remove the "Dowex-50," methanol was distilled off from the filtrate, and the distilled filtrate was purified by silica gel column chromatography ($CHCl_3$:MeOH=5:1) to yield 0.9 g of a deacetylated product (Rf=0.25 silica gel/$CHCl_3$:MeOH=5:1).

The deacetylated product was stirred together with 3 g of dipalmitoyl phosphatidylcholine at 30° C. for 6 hours in a mixed solvent comprising 120 ml of diethyl ether and 24 ml of water in the presence of 6 ml of 0.4 M calcium acetate and 100 units of "PLD" (manufactured by Asahi Chemical) to yield a crude product. The crude product was then purified by silica gel chromatography ($CHCl_3$:MeOH=9:1) to yield 0.3 g of an intermediate.

0.3 g of the obtained intermediate was dissolved in a mixed solvent comprising 10 ml of THF and 5 ml of $H_2O$. Under ice-cooling conditions, 0.3 ml of 1 N-NaOH solution was added, and the obtained mixture was stirred for one hour. After neutralizing the mixture (to pH 8) by adding "Dowex-50" ($H^+$ form), the reaction mixture was filtered to remove the "Dowex-50." The filtrate was concentrated and purified by column chromatography (ODS/$H_2O$, MeOH) to yield 9.6 mg of the desired sialic acid derivative, i.e., a sialylphospholipid of the general formula (2), wherein $X^3$ represents an N-acetylneuraminic acid residue, $R^2$ and $R^3$ both represent palmitoyl groups, and n is 8.

When this sialylphospholipid was subjected to a TLC analysis, it showed a single spot, and positively responded to both Ditmmer reagent and resorcinol reagent. Instrumental analysis values were as follows: 1H-NMR ($CD_3OD$, 400 MHz) δ0.896 (6H, t, J=6.9 Hz), δ1.327 (56H, m), δ1.525 (4H, m), δ1.616 (4H, m), δ1.729 (1H, t, J=12.4 Hz), δ1.997 (3H, s), δ2.310 (2H, t, J=7.4 Hz), δ2.326 (2H, t, J=7.4 Hz), δ2.674 (1H, dd, J=13.2, 4.7 Hz), δ3.997 (2H, t, J=6.0 Hz), δ4.141 (1H, dd, J=12.1, 7.1 Hz), δ4.436 (1H, dd, J=12.1, 3.3 Hz), δ5.247 (1H, m). Molecular weight: 1067. This sialic acid derivative is hereinafter referred to as "Sialylphospholipid 1."

Production Example 2
Preparation of N-Acetylneuraminylphospholipid 4.39 g of 1,8-octanediol was dissolved in 200 ml of chloroform, and 7.90 g of soybean hydrogenated phosphatidylcholine (manufactured by Taiyo Kagaku) was added to the above mixture. Thirty ml of an acetic acid buffer solution (pH 5.6) and 3 ml of 0.4 M calcium acetate aqueous solution were added to the above mixture. Further, 370 units of a PLD dissolved in the same buffer solution were gradually added to the above mixture, and then the obtained mixture was stirred for 50 hours at 30 to 35° C., to allow the components to react with one another. After the reaction was completed, the organic solvents were distilled off from the reaction mixture, and the distilled product was purified by silica gel column chromatography (AcOEt:$CHCl_3$=3:1) to yield 5.65 g of phosphatidyloctanol.

2.34 g of a benzyl ester of the peracetyl-2-chloro derivative of N-acetylneuraminic acid synthesized by the method described in Production Example 1 and 3.33 g of phosphatidyloctanol were dissolved in 200 ml of chloroform. Thereafter, 1.14 g of disodium hydrogen phosphate and 2.34 g of Molecular Sieve 4A were added to the above mixture. After cooling the above mixture to −50° C. to −40° C., a mixture of 1.03 g of silver trifluoromethanesulfonate dissolved in 15 ml of toluene was added dropwise to the above mixture. Thereafter, while gradually heating the mixture to room temperature, the mixture was stirred for one hour, to allow the components to react with one another. After the reaction mixture was filtered through Celite, the insoluble components were removed, to yield a filtrate. Thereafter, the organic solvents were distilled off from the filtrate. The residue was then purified by silica gel column chromatography ($CH_2Cl_2$:MeOH=20:1-1:1) to yield 900 mg of a methylated product of sialylphospholipid acetylated derivatives.

Two-hundred and thirty-four mg of the acetylated product of sialylphospholipid was dissolved in 70 ml of methanol. Under ice-cooling, 30%-methanol solution of potassium methoxide (MeOK 42 mg/MeOH 100 mg) was gradually added dropwise to the above mixture. After the completion of reaction, the mixture was neutralized (to pH 8) by adding "Dowex-50" ($H^+$ form), and then the reaction mixture was filtered to remove the "Dowex-50." The organic solvents were distilled off from the filtrate, and then the distilled filtrate was then purified by silica gel column chromatography ($CHCl_3$:MeOH=2:1) to yield 111 mg of a methylated product of sialylphospholipid. One-hundred mg of the methylated product of sialylphospholipid was dissolved in a mixed solvent comprising 30 ml of ethanol and 10 ml of chloroform. Twenty mg of 10% palladium activated charcoal was added to the above mixture, the obtained mixture was sufficiently blended by ultrasonic dispersion. Three drops of 0.01 N hydrochloric acid was added dropwise to the above mixture, and the hydrogen addition reaction was carried out for 24 hours while stirring the mixture under normal pressure. After the completion of the reaction, the pressure was dropped to a reduced pressure to remove hydrogen, replacing with nitrogen. After the reaction mixture was filtered through Celite, the palladium charcoal was removed, to give a filtrate. Thereafter, the organic solvents in the filtrate were distilled off, and the distilled filtrate was purified by preparative TLC ($CHCl_3$:MeOH:$H_2O$=70:30:5), to yield 43.2 mg of the desired sialic acid derivative, i.e., a sialylphospholipid of the general formula (2), wherein $X^3$ represents an N-acetylneuraminic acid residue, $R^2$ and $R^3$ both represent acyl groups of soybean hydrogenated phosphatidylcholine, and n is 8. This sialic acid derivative is hereinafter referred to as "Sialylphospholipid 2."

Production Example 3
Preparation of 1-Methoxycarbonyl-N-acetylneuraminylphospholipid Three grams of N-acetylneuraminic acid was dissolved in 300 ml of methanol. Three grams of "Dowex-50" ($H^+$ form) was added to the above mixture, and the obtained mixture was then stirred at room temperature for 4 hours. After completion of the reaction, the reaction mixture was filtered to remove the "Dowex-50." The filtrate methanol solution was concentrated to a volume of 15 ml. To this concentrate, 6 ml of diethyl ether was added at −20° C., to yield 2.47 g of a methylated product of N-acetylneuraminic acid by recrystallization.

To the methylated product thus obtained, 25 g of acetyl chloride and 3 g of acetic acid anhydride were added at −20° C. Subsequently, the reaction vessel was saturated with dry gaseous hydrogen chloride, and the obtained mixture was stirred at room temperature for 20 hours. After the solvent was distilled off, the reaction mixture was completely dehydrated with benzene and toluene. This product was then recrystallized from a mixture comprising the equal amounts of dichloromethane, diethyl ether, and hexane to yield 3 g of an acetylated product.

This acetylated product was dissolved in 60 ml of dichloromethane containing 6 g of Molecular Sieve 4A, 5 g of $Ag_2CO_3$ and 3 g of 1,8-octanediol monomethyl ester, at −20° C., and the obtained mixture was stirred at room temperature for 3 hours, to carry out a glycosylation reaction. After the reaction mixture was filtered through Celite, the solvent was distilled off. The residue was then purified by silica gel column chromatography ($CH_2Cl_2$:MeOH= 98:2) to yield 1.9 g of a glycosylated product (Rf=0.63 silica gel/$CH_2Cl_2$:MeOH=15:1).

Under ice-cooling conditions, 1.9 g of the glycosylated product was dissolved in 30 ml of completely dehydrated methanol. Under ice-cooling conditions, 300 mg of potassium was added to the completely dehydrated methanol to produce potassium methoxide, which was then added to a methanol solution of the previously prepared glycosylated product. After the reaction was carried out while the mixture was stirred at 0° C. for 3 hours, Dowex-50 ($H^+$ form) was added to the reaction mixture at −20° C. After the reaction mixture was filtered to remove the "Dowex-50," methanol was distilled off from the filtrate, and the distilled filtrate was purified by silica gel column chromatography ($CHCl_3$:MeOH=5:1) to yield 0.9 g of a deacetylated product (Rf=0.25 silica gel/$CHCl_3$:MeOH=5:1).

The deacetylated product was allowed to react with 3 g of dipalmitoyl phosphatidylcholine at 30° C. for 6 hours in a mixed solvent comprising 120 ml of diethyl ether and 24 ml of water in the presence of 6 ml of 0.4 M calcium acetate and 100 units of "PLD" to yield a crude product. The crude product was then purified by silica gel chromatography ($CHCl_3$:MeOH=9:1) to yield 0.3 g of the desired sialic acid derivative, i.e., a sialylphospholipid of the general formula (2), wherein $X^3$ represents a 1-methoxycarbonyl-N-acetylneuraminic acid residue, $R^2$ and $R^3$ both represent palmitoyl groups, and n is 8. This sialic acid derivative is hereinafter referred to as "Sialylphospholipid 3."

Production Example 4
Preparation of 9-O-Acetylneuraminylphospholipid

Four-hundred mg of 1,3-propanediol, 790 mg of distearoyl phosphatidylcholine (manufactured by Funakoshi), and 420 mg of 9-O-acetylneuraminic acid synthesized by a known method were used as starting materials. These starting materials were treated in the same manner as in Production Example 2, to yield 4.5 mg of the desired sialic acid derivative, i.e., a sialylphospholipid of the general formula (2), wherein $X^3$ represents a 9-O-acetylneuraminic acid residue, $R^2$ and $R^3$ both represent stearoyl groups, and n is 3. This sialic acid derivative is hereinafter referred to as "Sialylphospholipid 4."

Production Example 5
Preparation of 4-O-Acetylneuraminylphospholipid

Four-hundred and twenty mg of 1,4-butanediol, 765 mg of dimyristoyl phosphatidylcholine (manufactured by Funakoshi), and 420 mg of 4-O-acetylneuraminic acid synthesized by a known method were used as starting materials. These starting materials were treated in the same manner as in Production Example 2, to yield 4.7 mg of the desired sialic acid derivative, i.e., a sialylphospholipid of the general formula (2), wherein $X^3$ represents a 4-O-acetylneuraminic acid residue, $R^2$ and $R^3$ both represent myristoyl groups, and n is 4. This sialic acid derivative is hereinafter referred to as "Sialylphospholipid 5."

Production Example 6
Preparation of 3'-Sialyllactosylphospholipid

Two-hundred and forty mg of 1,6-hexanediol, 400 mg of stearoyl lysophosphatidylcholine (manufactured by Funakoshi), and 200 mg of 3'-sialyllactose were used as starting materials. These starting materials were treated in the same manner as in Production Example 2, to yield 2.2 mg of the desired sialic acid derivative, i.e., a sialylphospholipid of the general formula (2), wherein $X^3$ represents a 3'-sialyllactose residue, $R^2$ represents a stearoyl group, $R^3$ represents a hydrogen atom, and n is 6. This sialic acid derivative is hereinafter referred to as "Sialylphospholipid 6."

Production Example 7
Preparation of 6'-Sialyllactosylphospholipid

Two-hundred eighty mg of 1,10-decanediol, 400 mg of dilinolenoyl phosphatidylcholine (manufactured by Funakoshi), and 200 mg of 6'-sialyllactose were used as starting materials. These starting materials were treated in the same manner as in Production Example 2, to yield 2.1 mg of the desired sialic acid derivative, i.e., a sialylphospholipid of the general formula (2), wherein $X^3$ represents a 6'-sialyllactose residue, $R^2$ and $R^3$ both represent linolenoyl groups, and n is 10. This sialic acid derivative is hereinafter referred to as "Sialylphospholipid 7."

Production Example 8
Preparation of N-Acetylneuraminylphospholipid

Two-hundred thirty mg of 1,8-octanediol, 250 mg of diarachidonoyl lecithin (manufactured by Funakoshi), and 200 mg of N-acetylneuraminic acid were used as starting materials. These starting materials were treated in the same manner as in Production Example 2, to yield 2.5 mg of the desired sialic acid derivative, i.e., a sialylphospholipid of the general formula (2), wherein $X^3$ represents an N-acetylneuraminic acid residue, $R^2$ and $R^3$ both represent arachidonoyl groups, and n is 8. This sialic acid derivative is hereinafter referred to as "Sialylphospholipid 8."

Production Example 9
Preparation of N-Acetylneuraminylphospholipid

Four-hundred forty mg of 1,8-octanediol, 790 mg of 1-palmitoyl-2-stearoyl lecithin (manufactured by Funakoshi), and 400 mg of N-acetylneuraminic acid were used as starting materials. These starting materials were treated in the same manner as in Production Example 2, to yield 4.5 mg of the desired sialic acid derivative, i.e., a sialylphospholipid of the general formula (2), wherein $X^3$ represents an N-acetylneuraminic acid residue, $R^2$ represents a palmitoyl group, $R^3$ represents a stearoyl group, and n is 8. This sialic acid derivative is hereinafter referred to as "Sialylphospholipid 9."

Production Example 10
Preparation of N-Acetylneuraminylphospholipid

Four-hundred forty mg of 1,8-octanediol, 790 mg of 1-stearoyl-2-palmitoyl lecithin (manufactured by Funakoshi), and 400 mg of N-acetylneuraminic acid were used as starting materials. These starting materials were treated in the same manner as in Production Example 2, to yield 4.3 mg of the desired sialic acid derivative, i.e., a sialylphospholipid of the general formula (2), wherein $X^3$ represents an N-acetylneuraminic acid residue, $R^2$ represents a stearoyl group, $R^3$ represents a palmitoyl group, and n is 8. This sialic acid derivative is hereinafter referred to as "Sialylphospholipid 10."

Example 1
Preparation of Monosialyloligosaccharides

Forty kilograms of a delipidated hen egg yolk (powder) was suspended in 200 liters of water, and the suspension was stirred at room temperature for 3 hours. After filtrating the above mixture, the mixture was incubated for two days at 4° C. to precipitate small amounts of insoluble substances, to obtain a supernatant. The obtained supernatant was concentrated to a volume of 20 liters using a reverse osmosis membrane ("NTR-7410," manufactured by Nitto Denko). After the pH of the obtained concentrate was adjusted to 5.0, 40 g of delipidated almond powder was added, and the obtained mixture was stirred at 37° C. for one day. After the obtained mixture was filtrated, and the filtrate was adsorbed to 100 liters of an anion exchange resin ("Dowex 1×8, "manufactured by Dow Chemical). After the adsorbed resin was washed with 200 liters of water, it was subjected to gradient elution using 0 to 0.15 M of AcONa aqueous solution. A 0 to 0.06 M fraction was concentrated, desalted, and then dried, to yield 1.4 g of monosialyloligosaccharides. When the purity of the obtained product was confirmed by HPLC, it was found to be 93%.

Example 2

Preparation of Disialyloligosaccharides

One-hundred kilograms of a delipidated hen egg yolk (powder) was suspended in 500 liters of water, and the suspension was stirred at room temperature for 3 hours. After filtrating the above mixture, the mixture was incubated for two days at 4° C. to precipitate small amounts of insoluble substances, to obtain a supernatant. The obtained supernatant was concentrated to a volume of 50 liters using the same reverse osmosis membrane as in Example 1. After the pH of the obtained concentrate was adjusted to 5.0, 700 g of delipidated almond powder was added, and the obtained mixture was stirred at 37° C. for one day. After the obtained mixture was filtrated, and the filtrate was adsorbed to 250 liters of the same anion exchange resin as in Example 1. After the adsorbed resin was washed with 500 liters of water, it was subjected to gradient elution using 0 to 0.3 M of NaCl solution. A 0.05 to 0.1 M NaCl eluent fraction was concentrated, desalted, and then dried, to yield 29.5 g of disialyloligosaccharides. When the purity of the obtained product was confirmed by HPLC, it was found to be 95%.

Example 3

Preparation of Disialyloligosaccharides

Similar procedures as in Example 2 were carried out to yield a concentrate of a volume of 50 liters. After the pH of the obtained concentrate was adjusted to 5.0, 700 g of delipidated apricot seed powder was added, and the obtained mixture was stirred at 37° C. for one day. After the obtained mixture was filtrated, and the filtrate was adsorbed to 250 liters of the same anion exchange resin as in Example 1. After the adsorbed resin was washed with 500 liters of water, it was subjected to gradient elution using 0 to 0.3 M of NaCl solution. A 0.05 to 0.1 M NaCl eluent fraction was concentrated, desalted, and then dried, to yield 27.2 g of disialyloligosaccharides. When the purity of the obtained product was confirmed by HPLC, it was found to be 92%.

Test Example 1

Confirmation of Oligosaccharide Chain Structure

The structure of the sugar chain of each oligosaccharide obtained in Examples 1 to 3 was confirmed. Specifically, the oligosaccharide obtained was derivatized with ABEE according to the method described in a literature (Journal of Food Science, 58, 743–747 (1993)), and the structure thereof was confirmed by Bio-Gel P-4 chromatography, HPLC, NMR, and a sugar composition analysis. Table 1 shows the data obtained by the NMR analysis.

TABLE 1

| Structure reporter group | | MS1 Measurements (ppm) | MS2 Measurements (ppm) | DS Measurements (ppm) |
| --- | --- | --- | --- | --- |
| H-1 | GlcNAc-2 | 4.629 | 4.624 | 4.625 |
|  | Man-3 | Not detected | Not detected | Not detected |
|  | Man-4 | 5.132 | 5.133 | 5.132 |
|  | Man-4' | 4.926 | 4.916 | 4.946 |
|  | GlcNAc-5 | 4.602 | 4.604 | 4.60 |
|  | GlcNAc-5' | 4.581 | 4.547 | 4.60 |
|  | Gal-6 | 4.445 | 4.444 | 4.442 |
|  | Gal-6' | 4.466 | — | 4.442 |
| H-2 | Man-3 | 4.237 | 4.235 | 4.240 |
|  | Man-4 | 4.192 | 4.188 | 4.193 |
|  | Man-4' | 4.108 | 4.099 | 4.115 |
| H-3a | NeuAc | 1.723 | 1.720 | 1.718 |
|  | NeuAc' | — | — | 1.718 |
| H-3e | NeuAc | 2.667 | 2.668 | 2.669 |
|  | NeuAc' | — | — | 2.669 |
| NAc | GlcNAc-1 | 1.902 | 1.903 | 1.903 |
|  | GlcNAc-2 | 2.071 | 2.067 | 2.071 |
|  | GlcNAc-5 | 2.068 | 2.065 | 2.071 |
|  | GlcNAc-5' | 2.044 | 2.048 | 2.062 |
|  | NeuAc | 2.028 | 2.028 | 2.028 |
|  | NeuAc' | — | — | 2.028 |

Notes)

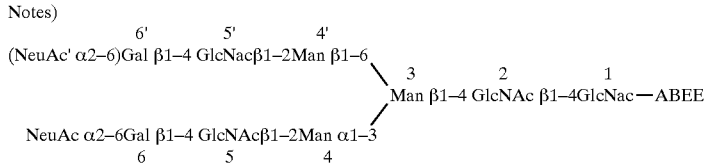

The HPLC analyses revealed that the oligosaccharide of Example 1 contained MS1 and MS2 of Table 1 as its main components, and the oligosaccharides of Examples 2 and 3 contained DS of Table 1 as their main component. By comparing the data in Table 1 with known data published in a literature (Journal of Food Science 58, 743–747 (1993)), it was revealed that the sugar chain structures of the oligosaccharide obtained in each Example are as follows:

Obtained in Example 1:

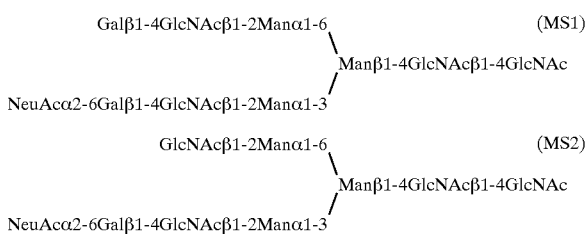

Obtained in Examples 2 and 3:

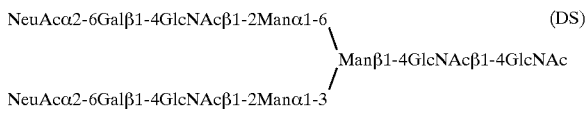

It is known that the main components of the sialyloligosaccharides in hen egg yolk are MS1, MS2, and DS mentioned above. (Journal of Food Science 58, 743–747 (1993)). Therefore, in spite of the presence of glycosidase, a desired oligosaccharide can readily be obtained without damages to the sugar structure by the method of the present invention. Incidentally, the mixture of MS1 and MS2 obtained in Example 1 is referred to as "MS."

Production Example 11
Preparation of Disialyloligosaccharide-phospholipid 4.5 g of 1,8-octanediol was dissolved in 200 ml of chloroform, and 6.8 g of dipalmitoyl phosphatidylcholine was added to the above mixture. Thirty ml of an acetic acid buffer solution (pH 5.6) and 3 ml of 0.4 M calcium acetate aqueous solution were added to the above mixture. Further, 370 units of a PLD dissolved in 0.5 ml of the same buffer solution (pH 5.6) were gradually added to the above mixture, and then the obtained mixture was stirred for 50 hours at 30° to 35° C., to allow the components to react with one another. After the reaction was completed, the organic solvents were removed from the reaction mixture, and the distilled product was purified by silica gel column chromatography (AcOEt:CHCl$_3$=3:1) to yield 5.5 g of phosphatidyloctanol.

Eighteen grams of disialyloligosaccharide obtained in Example 2 was dissolved in one liter of methanol. Ten grams of "Dowex-50" (H$^+$ form) was added to the above mixture, and the obtained mixture was then stirred at room temperature for 4 hours. After completion of the reaction, the reaction mixture was filtered to remove the "Dowex-50." The filtrate methanol solution was concentrated to a volume of 30 ml. To this concentrate, 10 ml of diethyl ether was added at –20° C., to yield 15.3 g of a methylated product of disialyloligosaccharide by recrystallization.

To the methylated product thus obtained, 25 g of acetyl chloride and 3 g of acetic acid anhydride were added at –20° C. Subsequently, the reaction vessel was saturated with dry gaseous hydrogen chloride, and the obtained mixture was stirred at room temperature for 24 hours. After the solvent was distilled off, the reaction mixture was completely dehydrated with benzene and toluene. This product was then recrystallized from a mixture comprising the equivalent amounts of dichloromethane, diethyl ether, and hexane to yield 16.2 g of an acetylated product.

This acetylated product was dissolved at –20° C. in 100 ml of dichloromethane containing 15 g of Molecular Sieve 4A, 10 g of Ag$_2$CO$_3$ and 5 g of phosphatidyloctanol obtained above, and the obtained mixture was stirred at room temperature for 4 hours, to carry out a glycosylation reaction. After the reaction mixture was filtered through Celite, the solvent was distilled off. The residue was then purified by silica gel column chromatography (CH$_2$Cl$_2$:MeOH=9:1) to yield 1.08 g of a methylated product of disialyloligosaccharide-phospholipid acetylated derivatives.

Five-hundred mg of the methylated product obtained above was dissolved in 100 ml of methanol. Under ice-cooling, 30%-methanol solution of potassium methoxide (MeOK 42 mg/MeOH 100 mg) was gradually added dropwise. After the completion of reaction, the mixture was neutralized by adding "Dowex-50" (H$^+$ form), and then the reaction mixture was filtered to remove the "Dowex-50." Thereafter, the organic solvents in the obtained filtrate was distilled off. The distilled filtrate was then purified by silica gel column chromatography (CHCl$_3$:MeOH=2:1) to yield 235 mg of a methylated product of disialyloligosaccharide-phospholipid.

Two-hundred mg of the methylated product obtained above was dissolved in a mixed solvent comprising 20 ml of THF and 10 ml of H$_2$O. Under ice-cooling conditions, 0.6 ml of 1N-NaOH solution was added to the above mixture, and the obtained mixture was stirred for one hour. The reaction mixture was neutralized by adding "Dowex-50" (H$^+$ form), and then the resin was washed by H$_2$O. The filtrate and the washing liquid were collectively concentrated, and the concentrated mixture was purified by column chromatography (ODS/H$_2$O,MeOH), to yield 20.1 mg of the desired sialic acid derivative, i.e., disialyloligosaccharide-phospholipid (DSPL3). When this disialyloligosaccharide-phospholipid was subjected to a TLC analysis, it showed a single spot, and positively responded to both Ditmmer reagent and resorcinol reagent.

Also, by changing the starting materials for the phospholipids and for the spacers, sialic acid derivatives with different acyl groups and spacers were obtained. Distearoyl phosphatidylcholine was used as a phospholipid, and 1,3-propanediol was used as a spacer to yield DSPL1. Dimyristoyl phosphatidylcholine was used as a phospholipid, and 1,4-butanediol was used as a spacer to yield DSPL2. Diarachidoyl phosphatidylcholine was used as a phospholipid, and 1,8-octanediol was used as a spacer to yield DSPL4. Dilinolenoyl phosphatidylcholine was used as a phospholipid, and 1,10-decanediol was used as a spacer to yield DSPL5. Each of the structures of the sialic acid derivatives is given below:

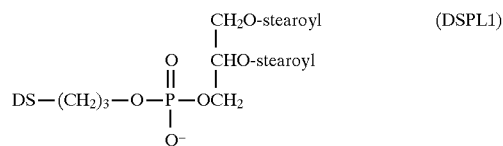

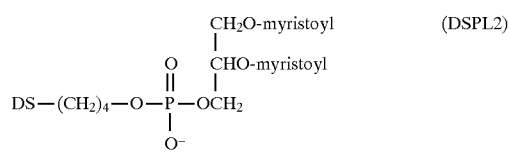

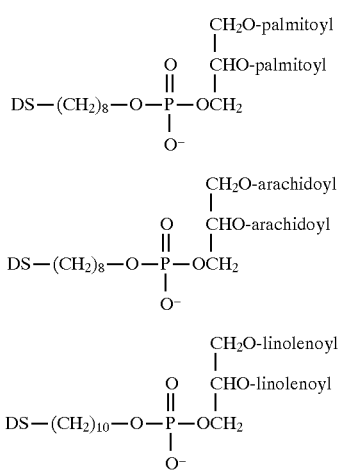

(DSPL3)
(DSPL4)
(DSPL5)

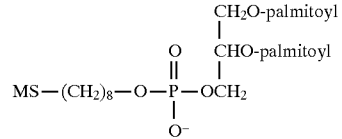

(MSPL3)
(MSPL4)
(MSPL5)

Production Example 12
Preparation of Monosialyloligosaccharide-phospholipid

Similar procedures as in Production Example 11 were carried out except for using the monosialyloligosaccharides (MS) obtained in Example 1, dipalmitoyl phosphatidylcholine, and 1,8-octanediol, to yield 20.1 mg of the desired sialic acid derivative, i.e., monosialyloligosaccharide-phospholipid (MSPL3).

Also, by changing the starting materials for the phospholipids and for the spacers, sialic acid derivatives with different acyl groups and spacers were obtained. Distearoyl phosphatidylcholine was used as a phospholipid, and 1,3-propanediol was used as a spacer to yield MSPL1. Dimyristoyl phosphatidylcholine was used as a phospholipid, and 1,4-butanediol was used as a spacer to yield MSPL2. Diarachidoyl phosphatidylcholine was used as a phospholipid, and 1,8-octanediol was used as a spacer to yield MSPL4. Dilinolenoyl phosphatidylcholine was used as a phospholipid, and 1,10-decanediol was used as a spacer to yield MSPL5. Each of the structures of the sialic acid derivatives is given below:

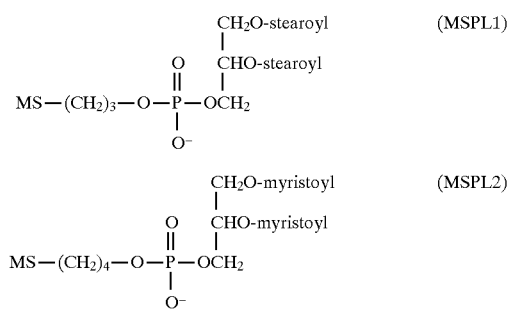

(MSPL1)
(MSPL2)

Production Example 13
Preparation of Sialyloligosaccharidepeptides

Fifty kilograms of a delipidated hen egg yolk (powder) was suspended in 250 liters of water, and the suspension was stirred at room temperature for 3 hours. After filtrating the above mixture, the mixture was incubated for two days at 4° C. to precipitate small amounts of insoluble substances, to obtain a supernatant. The obtained supernatant was concentrated to a volume of 50 liters using a reverse osmosis membrane (RO Membrane). The concentrate was adsorbed to 250 liters of an anion exchange resin ("MSA-1," manufactured by Dow Chemical). After the adsorbed resin was washed with 500 liters of water, it was subjected to elution using 50 mM of NaCl solution. Each of the water-washed fraction and the 50 mM NaCl eluent fraction was concentrated, desalted, and then dried, to respectively yield 5.6 g of monosialyloligosaccharide peptides (MS peptides) and 13.8 g of disialyloligosaccharide peptides (DS peptides). When the purities of the obtained products were confirmed by HPLC, they were found to be respectively 88% and 91%.

Test Example 2
Inhibitory Effect of Sialic Acid Derivatives on Influenza-Virus-Induced Hemagqlutination 0.25 mL of PBS containing each of the samples in Table 2 in varying concentrations shown in Table 2 was mixed with a 0.25 mL liquid containing influenza $A_2$ virus (4HA units), and the mixture was stirred at 37° C. for 30 minutes. After the mixture was incubated for 1 hour at room temperature, the hemagglutination ability of hen erythrocytes was determined. Using the test sample which was obtained from the animals that received PBS containing no sialic acid derivative as the control, the hemagglutination inhibition rate was determined. The results are shown in Table 2.

TABLE 2

| | Concentration ($\mu$g/mL) | | | | | |
|---|---|---|---|---|---|---|
| Sample | 100 | 50 | 25 | 12.5 | 6.25 | 3.125 |
| MS | 74 (%) | 57 (%) | 50 (%) | 28 (%) | 17 (%) | 9 (%) |
| DS | 89 | 70 | 65 | 38 | 24 | 15 |
| MSPL1 | 100 | 100 | 100 | 95 | 84 | 69 |
| MSPL2 | 100 | 100 | 100 | 91 | 78 | 60 |

TABLE 2-continued

| Sample | Concentration (μg/mL) | | | | | |
|---|---|---|---|---|---|---|
| | 100 | 50 | 25 | 12.5 | 6.25 | 3.125 |
| MSPL3 | 100 | 100 | 98 | 89 | 74 | 62 |
| MSPL4 | 100 | 97 | 100 | 87 | 76 | 59 |
| MSPL5 | 100 | 100 | 95 | 82 | 70 | 55 |
| DSPL1 | 100 | 100 | 100 | 100 | 94 | 85 |
| DSPL2 | 100 | 100 | 100 | 97 | 89 | 78 |
| DSPL3 | 100 | 100 | 100 | 91 | 81 | 72 |
| DSPL4 | 100 | 100 | 100 | 90 | 76 | 69 |
| DSPL5 | 100 | 100 | 97 | 89 | 74 | 60 |
| MS peptide | 72 | 54 | 41 | 29 | 16 | 7 |
| DS peptide | 84 | 69 | 62 | 37 | 20 | 12 |
| Sialylphospholipid 1 | 100 | 100 | 100 | 94.3 | 82.1 | 69.5 |
| Sialylphospholipid 2 | 100 | 100 | 100 | 100 | 92.3 | 80.3 |
| Sialylphospholipid 3 | 100 | 100 | 100 | 92.6 | 80.1 | 65.1 |
| Sialylphospholipid 4 | 100 | 100 | 100 | 100 | 95.5 | 84.3 |
| Sialylphospholipid 5 | 100 | 100 | 100 | 95.1 | 86.3 | 70.5 |
| Sialylphospholipid 6 | 100 | 100 | 100 | 100 | 91.4 | 83.0 |
| Sialylphospholipid 7 | 100 | 100 | 100 | 90.5 | 81.1 | 74.4 |
| Sialylphospholipid 8 | 100 | 100 | 100 | 92.2 | 79.3 | 68.6 |
| Sialylphospholipid 9 | 100 | 100 | 100 | 97.5 | 83.1 | 70.2 |
| Sialylphospholipid 10 | 100 | 100 | 100 | 94.4 | 82.5 | 71.5 |
| N-Acetylneuraminic acid | 63.3 | 47.1 | 35.5 | 20.9 | 12.4 | 4.3 |

As shown in Table 2, it was found that sialic acid derivatives, especially those bound to phospholipid, have an inhibitory effect on influenza-induced-hemagglutination. It was also found that the inhibitory effect of each sialic acid derivative was markedly higher than that of N-acetylneuraminic acid.

Test Example 3

Inhibitory Effect of Sialic Acid Derivatives on Rotavirus Infection

One hundred μl of Eagle's minimum essential medium (manufactured by Nissui, hereinafter referred to as EMEM) containing each of the samples in Table 3 in varying concentrations shown in Table 3 or each of the sialic acid derivatives (sialylphospholipids) obtained in Production Examples 2, 4, 6 and 8 and N-acetylneuraminic acid in concentrations of 100 mg/mL, 10 mg/mL, 1 mg/mL, 0.1 mg/mL, and 0.01 mg/mL was mixed with 100 μl of EMEM containing human rotavirus (MO cell line) and the mixture was incubated at 37° C. for 1 hour. The mixture was added to MA 104 cells (monkey kidney cells) which were grown to confluency in each well of a 96-well titre plate. The plate was incubated at 37° C. for 1 hour and then the liquid portion was removed. Then EMEM was added and incubated at 37° C. for further 17 hours. Then, after fixation with cooled methanol, the rotavirus infection rate was determined by staining the infected cells using an indirect fluorescent antibody technique. Using the control which was treated with EMEM containing no sialic acid derivatives instead of EMEM containing the above sialic acid derivatives, the rate of inhibition of rotavirus infection was determined. The results are shown in FIG. 1 and Table 3.

TABLE 3

| Sample | Concentration (mg/mL) | | | |
|---|---|---|---|---|
| | 1 | 0.1 | 0.01 | 0.001 |
| MS | 67.3 (%) | 60.6 (%) | 23.2 (%) | 10.3 (%) |
| DS | 69.5 | 68.8 | 39.1 | 15.3 |
| MSPL1 | 87.9 | 90.2 | 61.5 | 58.8 |

TABLE 3-continued

| Sample | Concentration (mg/mL) | | | |
|---|---|---|---|---|
| | 1 | 0.1 | 0.01 | 0.001 |
| MSPL2 | 91.0 | 82.4 | 80.9 | 54.1 |
| MSPL3 | 92.2 | 85.7 | 79.9 | 60.1 |
| MSPL4 | 90.3 | 83.5 | 75.7 | 60.8 |
| MSPL5 | 89.0 | 80.1 | 71.5 | 61.0 |
| DSPL1 | 90.5 | 92.2 | 83.1 | 70.5 |
| DSPL2 | 92.1 | 91.8 | 86.3 | 69.4 |
| DSPL3 | 100 | 95.4 | 92.6 | 84.3 |
| DSPL4 | 98.7 | 92.6 | 89.5 | 83.0 |
| DSPL5 | 99.1 | 94.3 | 83.1 | 74.4 |
| N-Acetylneuraminic acid | 20.9 | 12.3 | 7.8 | 2.2 |

As shown in FIG. 1 and Table 3, it was found that each of the sialic acid derivatives showed an inhibitory effect on rotavirus infection and that the inhibitory effect was markedly higher than that of N-acetylneuraminic acid.

Test Example 4

Inhibitory Effect of Sialic Acid Derivatives on Rotavirus Proliferation

A human rotavirus (MO cell line) was added to the cells of MA104 which were grown to confluency in a roller bottle, and cultured with shaking at 37° C. for 1 hour, whereby the cells of MA104 was infected with the rotavirus. After the infected cells were washed with EMEM, EMEM containing each of the samples in varying concentration listed in Table 4 was added to the roller bottle, which was then subjected to shaking culture at 37° C. for 3 days. With the supernatant of the culture, the infection titre of the rotavirus was determined by an indirect fluorescent antibody technique. The rate of inhibition of rotaviral proliferation was obtained, as compared with the control for which EMEM containing no sialic acid derivatives was used. The results are shown in Table 4.

TABLE 4

| Sample | Concentration | Rotaviral titre (%) |
|---|---|---|
| MS | 1 mg/mL | 28.7 |
| DS | 1 mg/mL | 12.0 |
| MSPL1 | 100 μg/mL | 8.3 |
| MSPL2 | 100 μg/mL | 7.1 |
| MSPL3 | 100 μg/mL | 10.0 |
| MSPL4 | 100 μg/mL | 9.8 |

0.25 mL of PBS containing each of the samples in varying concentrations listed in Table 5 was mixed with a 0.25 mL liquid containing Newcastle disease virus (4HA units), and the mixture was shaken at 37° C. for 30 minutes. After incubating for 1 hour at room temperature, the rate of inhibition of hemagglutination with hen erythrocytes was determined as compared with the control for which PBS containing no sialic acid derivatives was used. The results are shown in Table 5.

TABLE 5

| Sample | Concentration (μg/mL) | | | | | |
|---|---|---|---|---|---|---|
| | 100 | 50 | 25 | 12.5 | 6.25 | 3.125 |
| MS | 51 (%) | 46 (%) | 33 (%) | 20 (%) | 5 (%) | — |
| DS | 67 | 55 | 46 | 25 | 16 | — |
| MSPL1 | 100 | 100 | 83 | 69 | 44 | — |
| MSPL2 | 100 | 100 | 82 | 72 | 60 | — |
| MSPL3 | 100 | 100 | 85 | 82 | 72 | — |
| MSPL4 | 100 | 100 | 83 | 79 | 69 | — |
| MSPL5 | 100 | 100 | 90 | 77 | 65 | — |
| DSPL1 | 100 | 100 | 92 | 76 | 59 | — |
| DSPL2 | 100 | 100 | 95 | 80 | 64 | — |
| DSPL3 | 100 | 100 | 100 | 93 | 79 | — |
| DSPL4 | 100 | 100 | 100 | 92 | 80 | — |
| DSPL5 | 100 | 100 | 98 | 89 | 76 | — |
| Sialylphospholipid 1 | 100 | 100 | 97.2 | 83.3 | 71.5 | 60.4 (%) |
| Sialylphospholipid 2 | 100 | 100 | 100 | 92.5 | 78.8 | 64.7 |
| Sialylphospholipid 3 | 100 | 100 | 85.3 | 69.8 | 52.1 | 40.6 |
| Sialylphospholipid 4 | 100 | 100 | 93.2 | 72.1 | 59.6 | 44.3 |
| Sialylphospholipid 5 | 100 | 100 | 91.0 | 68.8 | 57.5 | 42.4 |
| Sialylphospholipid 6 | 100 | 100 | 100 | 89.5 | 72.0 | 59.7 |
| Sialylphospholipid 7 | 100 | 100 | 94.4 | 80.6 | 68.7 | 87.1 |
| Sialylphospholipid 8 | 100 | 100 | 90.3 | 78.6 | 62.3 | 47.7 |
| Sialylphospholipid 9 | 100 | 100 | 95.3 | 84.1 | 70.1 | 59.8 |
| Sialylphospholipid 10 | 100 | 100 | 92.4 | 80.5 | 67.2 | 60.7 |
| N-Acetylneuraminic acid | 46.3 | 30.1 | 18.8 | 5.7 | 0 | 0 |

TABLE 4-continued

| Sample | Concentration | Rotaviral titre (%) |
|---|---|---|
| MSPL5 | 100 μg/mL | 12.1 |
| DSPL1 | 100 μg/mL | 5.2 |
| DSPL2 | 100 μg/mL | 6.3 |
| DSPL3 | 100 μg/mL | 4.9 |
| DSPL4 | 100 μg/mL | 5.5 |
| DSPL5 | 100 μg/mL | 6.1 |
| Sialylphospholipid 1 | 100 μg/mL | 8 |
| Sialylphospholipid 2 | 100 μg/mL | 5 |
| Sialylphospholipid 3 | 100 μg/mL | 10 |
| Sialylphospholipid 4 | 100 μg/mL | 7 |
| Sialylphospholipid 5 | 100 μg/mL | 10 |
| Sialylphospholipid 6 | 100 μg/mL | 12 |
| Sialylphospholipid 7 | 100 μg/mL | 14 |
| Sialylphospholipid 8 | 100 μg/mL | 10 |
| Sialylphospholipid 9 | 100 μg/mL | 5 |
| Sialylphospholipid 10 | 100 μg/mL | 6 |
| N-Acetylneuraminic acid | 10 mg/mL | 15 |
| Not added | — | 100 |

As shown in Table 4, it was found that each of the sialic acid derivatives showed an inhibitory effect on rotaviral proliferation and that the inhibitory effect was markedly higher than that of N-acetylneuraminic acid.

Test Example 5

Antiviral Effect of Sialic Acid Derivatives on Newcastle Disease Virus

As shown in Table 5, it was found that each of the sialic acid derivatives showed an inhibitory effect on hemagglutination induced by Newcastle disease virus and that the inhibitory effect was markedly higher than that of N-acetylneuraminic acid.

Test Example 6

Anti-Viral Effect of Sialic Acid Derivatives on Herpes Virus 0.25 mL of EMEM containing each of the samples in varying concentrations listed in Table 6 was mixed with 0.25 mL of EMEM containing herpes simplex virus I, and incubated for 1 hour at 37° C. The mixture was added to the culture of Hela cells which had been grown to confluency in a mini bottle, and incubated at 37° C. for 1 hour. After the solution was decanted, EMEM was added to the residue and incubated for further 72 hours. Fixation was carried out by adding 10% formalin, and then the specimen was stained with crystal violet to count the number of plaques. The rate of inhibition of plaque formation was obtained, as compared with the control for which EMEM containing no sialic acid derivatives was used. The results are shown in Table 6.

TABLE 6

| Sample | Concentration, (μg/mL) | | | | | |
|---|---|---|---|---|---|---|
| | 1000 | 100 | 10 | 1 | 0.1 | 0.01 |
| MS | 35 (%) | 33 (%) | 29 (%) | 7 (%) | 0 (%) | 0 (%) |
| DS | 55 | 44 | 38 | 12 | 0 | 0 |
| MSPL1 | 100 | 100 | 88 | 69 | 53 | 33 |
| MSPL2 | 100 | 100 | 87 | 71 | 58 | 35 |
| MSPL3 | 100 | 100 | 81 | 66 | 52 | 31 |
| MSPL4 | 100 | 100 | 82 | 70 | 50 | 32 |
| MSPL5 | 100 | 94 | 79 | 65 | 43 | 29 |
| DSPL1 | 100 | 100 | 86 | 77 | 61 | 39 |
| DSPL2 | 100 | 100 | 90 | 83 | 60 | 44 |
| DSPL3 | 100 | 100 | 79 | 71 | 59 | 31 |
| DSPL4 | 100 | 100 | 78 | 67 | 57 | 33 |
| DSPL5 | 100 | 98 | 75 | 66 | 48 | 29 |
| Sialylphospholipid 1 | 100 | 100 | 90.2 | 72.8 | 53.1 | 33.6 |
| Sialylphospholipid 2 | 100 | 100 | 100 | 93.4 | 72.1 | 48.5 |
| Sialylphospholipid 3 | 100 | 100 | 84.8 | 70.3 | 59.5 | 44.3 |
| Sialylphospholipid 4 | 100 | 100 | 100 | 95.2 | 73.3 | 51.2 |
| Sialylphospholipid 5 | 100 | 100 | 100 | 89.5 | 59.6 | 38.1 |
| Sialylphospholipid 6 | 100 | 100 | 100 | 98.5 | 84.8 | 60.2 |
| Sialylphospholipid 7 | 100 | 100 | 100 | 90.3 | 78.6 | 53.1 |
| Sialylphospholipid 8 | 100 | 100 | 88.5 | 70.6 | 52.3 | 32.9 |
| Sialylphospholipid 9 | 100 | 100 | 96.1 | 74.3 | 55.4 | 31.3 |
| Sialylphospholipid 10 | 100 | 100 | 93.2 | 72.5 | 82.5 | 71.5 |
| N-Acetylneuraminic acid | 20.3 | 3.1 | 0 | 0 | 0 | 0 |

As shown in Table 6, it was found that the sialic acid derivatives, especially those bound to phospholipids, showed an antiviral effect on herpes virus, and that each of the sialic acid derivatives had a markedly higher inhibitory effect on plaque formation than N-acetylneuraminic acid.

Test Example 7

Inhibitory Effect of Sialic Acid Derivatives on *Helicobacter pylori* Adhesion

PBS containing each of the samples in varying concentrations listed in Table 4 was mixed with a suspension containing *Helicobacter pylori* in PBS ($2 \times 10^5$ CFU/mL), and the mixture was incubated at 37° C. for 30 minutes. Then, it was added to a 24-well plate coated with mucin (from pigs) and the plate was incubated at 37° C. for 2 hours. After the liquid portion was removed, the residue was washed with PBS, and the number of cells in the residue was determined by means of the indophenol method which uses the activity of urease secreted by the bacteria as the indicator. The rate of inhibition of bacterial adhesion was obtained, as compared with the control for which PBS containing no sialic acid derivatives was used. The results are shown in Table 7.

TABLE 7

| Sample | Concentration (mg/mL) | | | | |
|---|---|---|---|---|---|
| | 10 | 1 | 0.1 | 0.01 | 0.001 |
| MS | 56 (%) | 40 (%) | 29 (%) | 13 (%) | 0 (%) |
| DS | 62 | 49 | 38 | 18 | 2 |
| MSPL1 | 100 | 100 | 78 | 63 | 45 |
| MSPL2 | 100 | 98 | 77 | 60 | 41 |
| MSPL3 | 100 | 95 | 70 | 55 | 37 |
| MSPL4 | 100 | 93 | 66 | 57 | 32 |
| MSPL5 | 100 | 90 | 63 | 48 | 29 |
| DSPL1 | 100 | 100 | 87 | 70 | 49 |
| DSPL2 | 100 | 100 | 80 | 66 | 51 |
| DSPL3 | 100 | 94 | 72 | 54 | 38 |
| DSPL4 | 100 | 96 | 69 | 55 | 39 |
| DSPL5 | 100 | 91 | 65 | 51 | 30 |
| N-Acetylneuraminic acid | 29 | 14 | 3 | 0 | 0 |
| DS peptide | 58 | 42 | 37 | 17 | 0 |

As shown in Table 7, it was found that the sialic acid derivatives, especially those bound to phospholipids, showed an inhibitory effect on *Helicobacter pylori* adhesion, and that each of the sialic acid derivatives had a markedly higher inhibitory effect on the adhesion than N-acetylneuraminic acid.

Test Example 8

Anti-inflammatory Effect of Sialic Acid Derivatives (Effect on Carrageenin-Induced Knee Edema)

Male Wister rats (aged 8 weeks) were injected intravenously with 2 mL of Evans Blue/saline mixture (10 mg/mL), and then injected into the joint cavity of the right knee with 0.1 mL of 2% carrageenin/saline. Fifteen minutes before the injection of carrageenin, 100 µL, 10 µL and 1 µL of each of the samples in Table 8 dissolved in 100 µL of saline, or 100 µL of only saline, as a control, were injected into the joint cavity. Four hours later, the rats were killed, skinned to expose the knee joint, and observed for the infiltration of Evans Blue. Then, 0.15 mL of saline was injected into the joint cavity, and the joint was opened to collected 5 mL of the fluid in the cavity. The number of cells in the obtained fluid was counted, and calculated the rate of inhibition by regarding the number of cells in the control as 100% according to the following equation:

$$\text{Inhibition Rate (\%)} = \frac{\text{(No. of cells in the control)} - \text{(No. of cells after injection with a sample)}}{\text{(No. of cells in the control)}} \times 100$$

The results are shown in Table 8.

TABLE 8

| Sample | Concentration (µg/100 µL) | | |
|---|---|---|---|
|  | 1 | 10 | 100 |
| MS | 9.5 (%) | 21.8 (%) | 57.3 (%) |
| DS | 20.1 | 55.8 | 73.3 |
| MSPL3 | 15.4 | 29.7 | 60.2 |
| DSPL3 | 25.6 | 63.9 | 74.9 |
| N-Acetylneuraminic acid | 8.1 | 13.4 | 41.8 |

As shown in Table 8, it was found that the sialic acid derivatives had an anti-inflammatory effect, and that each of the sialic acid derivatives had a markedly higher anti-inhibitory effect than N-acetylneuraminic acid.

Test Example 9

Anti-allergic Effect of Sialic Acid Derivatives (Effect on the PCA (Passive Cutaneous Anaphylaxis) Reaction)

Male Hartlay guinea pigs, weighing 300 to 400 g, was intracutaneously injected with 0.1 mL of $16 \times 10^3$ dilution or $8 \times 10^4$ dilution of an antiserum (rabbit Ig G with an antibody titer of not less than 1/36000). Four hours later, a PCA reaction was provoked by an intravenous injection with an antigen solution containing 10 mg/kg of an antigen (ovalbumin) in 2 mL of 1% Evans Blue. Then, the guinea pigs were killed and skinned to measure the area of pigment infiltration. The amount of the pigment in the skin portion stained blue was measured by spectrometry (620 nm) according to the method of Katayama (Microbiol. Immunol., 22 89(1978)) to obtain the concentration of extracted pigment. Thirty minutes before the provocation of the PCA reaction, that is, 3.5 hours after the sensitization with the antiserum, each sialic acid derivative or saline was intravenously injected to the guinea pigs in the groups listed below, and the effect of the sialic acid derivatives upon the PCA reaction was observed. The results were expressed in percentages based upon the measurements in Group V. The results are shown in Table 9.

TABLE 9

| Group | Sample dose (mg/kg body weight) | Pigment infiltration area | | Concentration of extracted pigment | |
|---|---|---|---|---|---|
|  |  | 1/16000* | 1/80000* | 1/16000* | 1/80000* |
| I | 1 | 75.6 | 78.2 | 120.2 | 97.9 |
|  | 5 | 42.0 | 39.7 | 90.5 | 52.6 |
|  | 10 | 28.1 | 35.1 | 69.4 | 45.3 |

TABLE 9-continued

| Group | Sample dose (mg/kg body weight) | Pigment infiltration area | | Concentration of extracted pigment | |
|---|---|---|---|---|---|
|  |  | 1/16000* | 1/80000* | 1/16000* | 1/80000* |
| II | 1 | 68.8 | 53.3 | 87.4 | 61.2 |
|  | 5 | 20.9 | 21.4 | 30.5 | 18.8 |
|  | 10 | 18.8 | 15.4 | 20.0 | 13.9 |
| III | 1 | 57.7 | 50.1 | 43.3 | 37.1 |
|  | 5 | 17.6 | 12.9 | 22.1 | 15.4 |
|  | 10 | 18.8 | 13.8 | 23.9 | 20.5 |
| IV | 1 | 12.2 | 9.90 | 10.7 | 8.80 |
|  | 5 | 10.2 | 11.9 | 10.5 | 5.30 |
|  | 10 | 13.1 | 10.0 | 11.1 | 6.12 |
| VI | 1 | 81.4 | 83.9 | 128.6 | 99.1 |
|  | 5 | 63.7 | 59.5 | 89.5 | 80.7 |
|  | 10 | 38.4 | 32.3 | 47.4 | 41.3 |

*Dilution ratio

As shown in Table 9, it was found that the sialic acid derivatives had an anti-allergic effect, and that each of the sialic acid derivatives had a markedly higher anti-allergic effect than N-acetylneuraminic acid.

The kinds and doses of the samples used in each group are as follows:

Group I: MS was given in doses of 1 mg/kg body weight, 5 mg/kg body weight, and 10 mg/kg body weight;

Group II: DS was given in doses of 1 mg/kg body weight, 5 mg/kg body weight, and 10 mg/kg body weight;

Group III: MSPL3 was given in doses of 1 mg/kg body weight, 5 mg/kg body weight and 10 mg/kg body weight;

Group IV: DSPL3 was given in doses of 1 mg/kg body weight, 5 mg/kg body weight, and 10 mg/kg body weight;

Group V: 1 mL/kg body weight of saline was given; and

Group VI: N-acetylneuraminic acid was give in doses of 1 mg/kg of body weight, 5 mg/kg body weight, and 10 mg/kg body weight.

Test Example 10

Promoting Effect on Bifidobacteria Proliferation

To the following medium shown below, 500 mg/mL of each of the samples listed in Table 10 was added, where each of 5 bacterial cells, i.e., *B. adolescentis, B. breve, B. infantis, B. longum*, and *E. coli*, was inoculated and cultured at 37° C. under anaerobic conditions for 5 days. The degree of proliferation of the bacteria was evaluated by measuring turbidity at 600 nm. Regarding the turbidity of each culture grown on the medium containing 500 mg/mL of glucose instead of the samples as 100%, the proliferation rate was calculated. The results are shown e 10.

TABLE 10

| Sample | Cell line | Proliferation rate (%) |
|---|---|---|
| MS | B. adolescentis | 63.5 |
|  | B. breve | 59.7 |
|  | B. infantis | 80.1 |
|  | B. longum | 61.1 |
|  | E. coli | 38.7 |
| DS | B. adolescentis | 60.4 |
|  | B. breve | 58.2 |
|  | B. infantis | 76.8 |
|  | B. longum | 65.5 |
|  | E. coli | 22.1 |

TABLE 10-continued

| Sample | Cell line | Proliferation rate (%) |
|---|---|---|
| DS peptide | B. adolescentis | 57.1 |
|  | B. breve | 58.2 |
|  | B. infantis | 69.8 |
|  | B. longum | 67.3 |
|  | E. coli | 25.8 |
| N-Acetylneuraminic acid | B. adolescentis | 28.3 |
|  | B. breve | 21.5 |
|  | B. infantis | 32.8 |
|  | B. longum | 19.8 |
|  | E. coli | 25.4 |

The composition of the medium was as follows:

| | |
|---|---|
| $(NH_4)_2SO_4$ | 0.9 g |
| $KH_2PO_4$ | 0.45 g |
| $K_2HPO_4$ | 0.075 g |
| $MgSO_4.7H_2O$ | 0.09 g |
| NaCl | 0.9 g |
| $CaCl_2.2H_2O$ | 0.09 g |
| Trypticase (BBL) | 10 g |
| Yeast extract (Difco) | 5 g |
| Meat extract (Difco) | 2 g |
| Haemin | 0.007 g |
| $Na_2CO_3$ | 4 g |
| L-cysteine-hydrochloric acid salt-hydrate | 0.3 g |
| Distilled water | 1000 mL |
| pH 7.2 | |

As shown in Table 10, it was found that the sialic acid derivatives had a promoting effect on proliferation of Bifidobacteria. Each of the sialic acid derivatives had a markedly higher proliferation promoting effect than N-acetylneuraminic acid.

Figure 2:
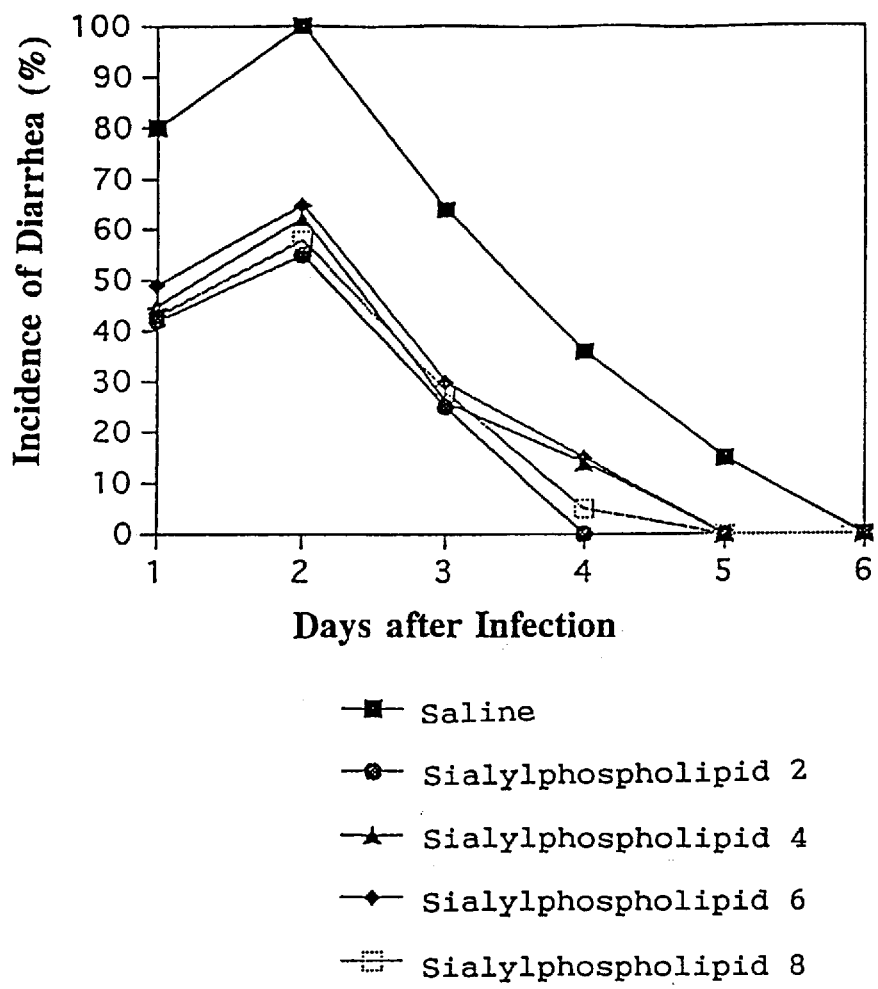
FIG. 2 shows a prophylactic effect of a sialic acid derivative (sialylphospholipid) on diarrhea caused by rotavirus.

Test Example 11
Prophylactic Effect of Sialic Acid Derivatives on Diarrhea Caused by Rotavirus Each of the sialic acid derivatives (sialylphospholipids) prepared in Production Examples 2, 4, 6, and 8 was diluted with saline to make a concentration of 1.0 mg/mL, 50 µL of which was orally given to each ddY mice aged 5 days. One hour after the administration of the sialic acid derivative solutions, each of the mice was orally infected with 50 µl of a diluted rotaviral EMEM solution having a rotaviral concentration sufficient to cause infection in the mouse. Then, occurrence of diarrhea was observed for 5 days. The results are shown in FIG. 2. The incidence of diarrhea was markedly lower in the sialic acid derivative administration group than in the non-administration group, indicating an excellent prophylactic effect of the sialic acid derivatives on rotaviral diarrhea.

Figure 3:
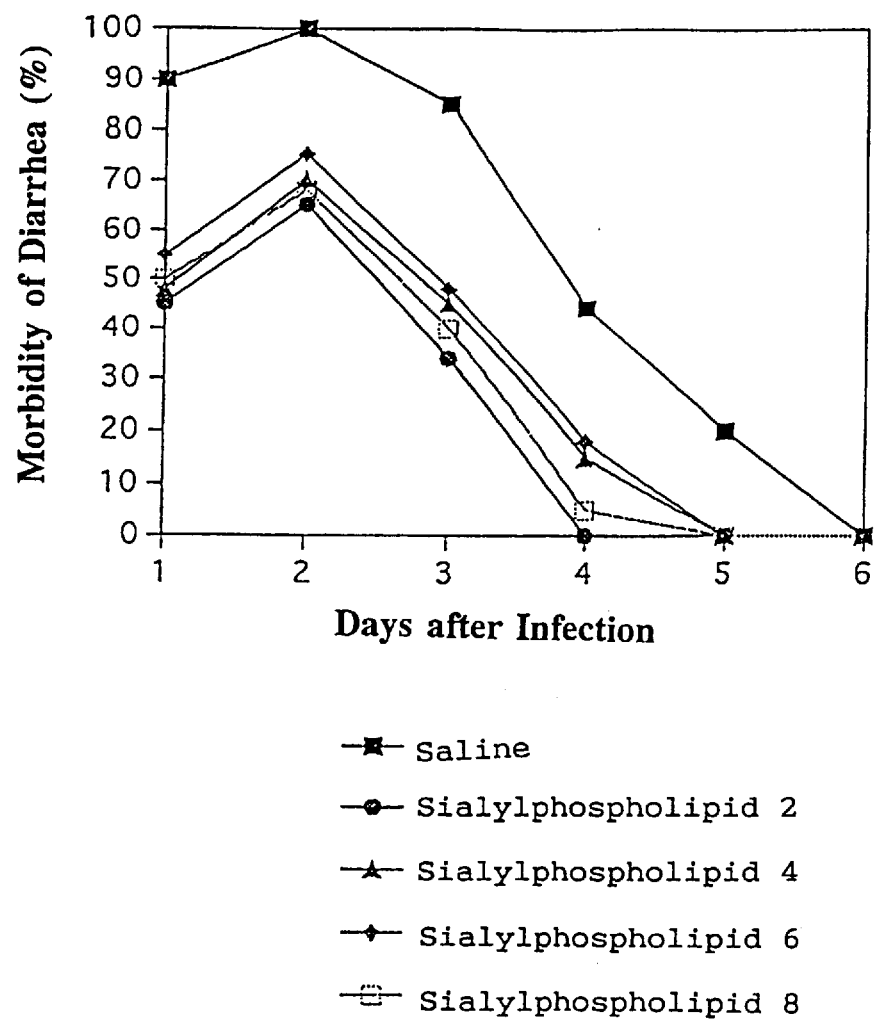
FIG. 3 shows a therapeutic effect of a sialic acid derivative (sialylphospholipid) on diarrhea caused by rotavirus.

Test Example 12
Therapeutic Effect of Sialic Acid Derivatives on Diarrhea Caused by Rotavirus ddY mice aged 5 days were orally infected with 50 µl of a diluted rotaviral EMEM solution having a rotaviral concentration sufficient to cause infection in the mouse. Then, each of the sialic acid derivatives (sialylphospholipids) prepared in Production Examples 2, 4, 6, and 8 was diluted with saline to make a concentration of 1.0 mg/mL, 50 µL of which was orally given to each mouse for 3 days. Then, occurrence of diarrhea was observed for 5 days, and the morbidity was calculated. The results are shown in FIG. 3. The morbidity of diarrhea was markedly lower and the recovery of the mice was more rapid in the sialic acid derivative administration group than in the non-administration group. Thus, the sialic acid derivatives had an excellent therapeutic effect on rotaviral diarrhea.

Test Example 13
Therapeutic Effect of Sialic Acid Derivatives on Diarrhea Caused by Salmonella Bacteria One hundred twenty calves infected with *Salmonella dublin* were divided into 12 groups of 10 animals each. In 11 groups, the animals were given every day milk formulation containing one of the sialic acid derivatives (sialylphospholipids) produced in Production Examples 1 to 10 or N-acetylneuraminic acid in an amount of 100 mg/day, and the remaining 1 group received the same amount of milk formulation containing no sialic acid derivatives in a similar way of feeding. The animals were kept on the above feed for 5 weeks, during which fecal score as an index for diarrhea and cell number of *Salmonella dublin* in feces were determined. The results are shown in Tables 11 and 12.

TABLE 11

| | Fecal score | | | | | |
|---|---|---|---|---|---|---|
| | Week 0 | Week 1 | Week 2 | Week 3 | Week 4 | Week 5 |
| Group receiving only milk formulation | 3 | 3 | 3 | 3 | 3 | 3 |
| Group receiving milk formulation containing N-acetylneuraminic acid | 3 | 2 | 2 | 2 | 2 | 1 |
| Group receiving milk formulation containing Sialylphospholipid 1 | 3 | 2 | 0 | 0 | 0 | 0 |
| Group receiving milk formulation containing Sialylphospholipid 2 | 3 | 1 | 0 | 0 | 0 | 0 |
| Group receiving milk formulation containing Sialylphospholipid 3 | 3 | 3 | 1 | 0 | 0 | 0 |
| Group receiving milk formulation containing Sialylphospholipid 4 | 3 | 2 | 0 | 0 | 0 | 0 |
| Group receiving milk formulation containing Sialylphospholipid 5 | 3 | 2 | 0 | 0 | 0 | 0 |
| Group receiving milk formulation containing Sialylphospholipid 6 | 3 | 1 | 0 | 0 | 0 | 0 |
| Group receiving milk formulation containing Sialylphospholipid 7 | 3 | 1 | 0 | 0 | 0 | 0 |

TABLE 11-continued

| | Fecal score | | | | | |
|---|---|---|---|---|---|---|
| | Week 0 | Week 1 | Week 2 | Week 3 | Week 4 | Week 5 |
| Group receiving milk formulation containing Sialylphospholipid 8 | 3 | 2 | 1 | 0 | 0 | 0 |
| Group receiving milk formulation containing Sialylphospholipid 9 | 3 | 2 | 0 | 0 | 0 | 0 |
| Group receiving milk formulation containing Sialylphospholipid 10 | 3 | 2 | 0 | 0 | 0 | 0 |

Means for 10 animals. Normal feces were given a score of 0; soft feces, 1; muddy feces, 2; and watery feces, 3.

TABLE 12

| | Cell number of *Salmonella dublin* in feces | | | | | |
|---|---|---|---|---|---|---|
| | Week 0 | Week 1 | Week 2 | Week 3 | Week 4 | Week 5 |
| Group receiving only milk formulation | 3.35 | 3.33 | 3.35 | 3.34 | 3.30 | 3.32 |
| Group receiving milk formulation containing N-Acetylneuraminic acid | 3.34 | 3.12 | 2.95 | 2.68 | 2.66 | 2.72 |
| Group receiving milk formulation containing Sialylphospholipid 1 | 3.37 | 2.51 | 2.45 | 2.28 | 2.05 | 1.94 |
| Group receiving milk formulation containing Sialylphospholipid 2 | 3.32 | 2.70 | 2.43 | 2.26 | 2.01 | 1.89 |
| Group receiving milk formulation containing Sialylphospholipid 3 | 3.36 | 2.87 | 2.66 | 2.58 | 2.47 | 2.36 |
| Group receiving milk formulation containing Sialylphospholipid 4 | 3.34 | 2.66 | 2.44 | 2.30 | 2.21 | 2.01 |
| Group receiving milk formulation containing Sialylphospholipid 5 | 3.36 | 2.72 | 2.48 | 2.29 | 2.08 | 2.00 |
| Group receiving milk formulation containing Sialylphospholipid 6 | 3.35 | 2.68 | 2.42 | 2.28 | 2.12 | 2.01 |
| Group receiving milk formulation containing Sialylphospholipid 7 | 3.36 | 2.76 | 2.52 | 2.38 | 2.18 | 2.03 |
| Group receiving milk formulation containing Sialylphospholipid 8 | 3.37 | 2.77 | 2.58 | 2.40 | 2.22 | 2.03 |
| Group receiving milk formulation containing Sialylphospholipid 9 | 3.34 | 2.61 | 2.42 | 2.19 | 2.09 | 1.95 |
| Group receiving milk formulation containing Sialylphospholipid 10 | 3.33 | 2.58 | 2.47 | 2.31 | 2.15 | 2.08 |

Means for 10 animals. No of cells per 1 g of feces was expressed in logarithmic value.

As shown in Tables 11 and 12, the fecal score and cell numbers of *Salmonella dublin* in feces were lower in the groups that received the milk formulation containing a sialic acid derivative than those in the group that received milk formulation containing no sialic acid derivative. From these findings, it was revealed that the sialic acid derivatives have an excellent therapeutic effect on diarrhea caused by *Salmonella dublin* infection. Each of the sialic acid derivatives showed a markedly higher therapeutic effect than N-acetylneuraminic acid.

Test Example 14
Therapeutic Effect of Sialic Acid Derivatives on Non-infectious Diarrhea Sixty calves were divided into 6 groups of 10 animals each. In 5 of the 6 groups, each animal was given daily milk formulation containing one of the sialic acid derivatives (sialylphospholipids) produced in Production Examples 2, 4, 6 and 8, or N-acetylneuraminic acid in an amount of 100 mg/day, and the remaining 1 group received in a similar way the same amount of milk formulation containing no sialic acid derivatives. The animals were kept on the above feed for 5 weeks, during which fecal score as an index for non-infectious diarrhea and cell counts of intestinal bacterial flora were determined. The results are shown in Tables 13 to 17. As for the group receiving N-acetylneuraminic acid, only fecal score is shown in the tables.

TABLE 13

| | Fecal score | | | | | |
|---|---|---|---|---|---|---|
| | Week 0 | Week 1 | Week 2 | Week 3 | Week 4 | Week 5 |
| Group receiving only milk formulation | 3 | 3 | 2 | 3 | 2 | 2 |
| Group receiving milk formulation containing N-acetyneuraminic acid | 3 | 2 | 2 | 1 | 2 | 2 |

TABLE 13-continued

| | Fecal score | | | | | |
|---|---|---|---|---|---|---|
| | Week 0 | Week 1 | Week 2 | Week 3 | Week 4 | Week 5 |
| Group receiving milk formulation containing Sialylphospholipid 2 | 3 | 1 | 0 | 0 | 0 | 0 |
| Group receiving milk formulation containing Sialylphospholipid 4 | 3 | 1 | 0 | 0 | 0 | 0 |
| Group receiving milk formulation containing Sialylphospholipid 6 | 3 | 1 | 0 | 0 | 0 | 0 |
| Group receiving milk formulation containing Sialylphospholipid 8 | 3 | 1 | 0 | 0 | 0 | 0 |

Means for 10 animals. Normal feces were given a score of 0; soft feces, 1; muddy feces, 2; and watery feces, 3.

TABLE 14

| | Intestinal bacterial flora | | | | | | |
|---|---|---|---|---|---|---|---|
| | | Week 0 | Week 1 | Week 2 | Week 3 | Week 4 | Week 5 |
| Group receiving only milk formulation | Total bacterial number | 10.5 | 10.1 | 9.7 | 9.9 | 9.7 | 9.6 |
| | Bacteroidaceae | 9.7 | 9.5 | 8.9 | 9.1 | 8.8 | 8.5 |
| | Bifidobacterium | 7.0 | 6.9 | 6.5 | 6.7 | 6.3 | 5.9 |
| | *Clostridium perfrigens* | 4.9 | 4.6 | 4.4 | 4.8 | 4.1 | 4.2 |
| | Enterobacteriaceae | 8.5 | 8.2 | 7.8 | 7.4 | 6.9 | 6.6 |
| | Lactobacillus | 6.0 | 5.4 | 5.2 | 4.8 | 4.9 | 4.5 |
| | Streptococcus | 6.8 | 6.6 | 6.1 | 5.4 | 5.2 | 4.8 |
| | Staphylococcus | 4.5 | 4.2 | 3.7 | 3.4 | 3.1 | 2.7 |
| Group receiving milk formulation containing Sialyl-phospholipid 2 | Total bacterial number | 10.1 | 10.3 | 9.8 | 9.7 | 9.8 | 9.6 |
| | Bacteroidaceae | 9.3 | 9.5 | 9.3 | 9.1 | 8.9 | 9.0 |
| | Bifidobacterium | 6.7 | 6.9 | 7.2 | 7.0 | 7.1 | 6.9 |
| | *Clostridium perfrigens* | 4.8 | 4.6 | 4.4 | 4.5 | 4.3 | 4.2 |
| | Enterobacteriaceae | 8.4 | 8.2 | 8.1 | 8.2 | 8.0 | 8.1 |
| | Lactobacillus | 5.5 | 5.7 | 5.8 | 5.7 | 5.6 | 5.7 |
| | Streptococcus | 6.7 | 6.5 | 6.5 | 6.3 | 6.1 | 5.9 |
| | Staphylococcus | 4.3 | 4.1 | 3.9 | 3.7 | 3.7 | 3.5 |

Means for 10 animals. No. of cell per 1 g of feces was expressed in logarithmic value.

TABLE 15

| | Intestinal bacterial flora | | | | | | |
|---|---|---|---|---|---|---|---|
| | | Week 0 | Week 1 | Week 2 | Week 3 | Week 4 | Week 5 |
| Group receiving milk formulation containing Sialyl-phospholipid 4 | Total bacterial number | 10.5 | 10.4 | 10.1 | 9.8 | 9.7 | 9.6 |
| | Bacteroidaceae | 9.4 | 9.3 | 9.2 | 9.2 | 9.3 | 9.1 |
| | Bifidobacterium | 6.8 | 6.8 | 6.9 | 7.1 | 7.0 | 7.1 |
| | *Clostridium perfrigens* | 4.9 | 4.8 | 4.6 | 4.5 | 4.4 | 4.3 |
| | Enterobacteriaceae | 8.6 | 8.5 | 8.3 | 8.3 | 8.2 | 8.2 |
| | Lactobacillus | 5.9 | 5.9 | 6.1 | 6.0 | 6.1 | 61 |
| | Streptococcus | 6.8 | 6.6 | 6.7 | 6.5 | 6.4 | 6.2 |
| | Staphylococcus | 4.4 | 4.2 | 4.1 | 4.1 | 3.9 | 3.8 |

Means for 10 animals. No. of cells per 1 g of feces was expressed in logarithmic value.

TABLE 16

| | | Intestinal bacterial flora | | | | | |
|---|---|---|---|---|---|---|---|
| | | Week 0 | Week 1 | Week 2 | Week 3 | Week 4 | Week 5 |
| Group receiving milk formulation containing Sialyl- phospholipid 6 | Total bacterial number | 10.3 | 10.1 | 10.2 | 9.9 | 9.7 | 9.5 |
| | Bacteroidaceae | 9.5 | 9.3 | 9.3 | 9.1 | 9.2 | 9.0 |
| | Bifidobacterium | 7.1 | 7.3 | 7.3 | 7.2 | 7.3 | 7.2 |
| | *Clostridium perfrigens* | 4.9 | 4.6 | 4.5 | 4.5 | 4.4 | 4.5 |
| | Enterobacteriaceae | 8.4 | 8.3 | 8.1 | 8.0 | 8.1 | 8.1 |
| | Lactobacillus | 5.9 | 6.0 | 6.1 | 6.1 | 6.0 | 6.1 |
| | Streptococcus | 6.6 | 6.4 | 6.3 | 6.1 | 6.0 | 6.0 |
| | Staphylococcus | 4.4 | 4.1 | 4.2 | 4.0 | 3.8 | 3.7 |

Means for 10 animals. No. of cells per 1 g of feces was expressed in logarithmic value.

TABLE 17

| | | Intestinal bacterial flora | | | | | |
|---|---|---|---|---|---|---|---|
| | | Week 0 | Week 1 | Week 2 | Week 3 | Week 4 | Week 5 |
| Group receiving milk formulation containing Sialyl- phospholipid 8 | Total bacterial number | 10.3 | 10.1 | 9.8 | 9.7 | 9.7 | 9.6 |
| | Bacteroidaceae | 9.5 | 9.3 | 9.3 | 9.1 | 9.2 | 9.1 |
| | Bifidobacterium | 6.9 | 7.1 | 7.3 | 7.3 | 7.2 | 7.2 |
| | *Clostridium perfrigens* | 4.8 | 4.7 | 4.5 | 4.4 | 4.2 | 4.2 |
| | Enterobacteriaceae | 8.5 | 8.3 | 8.2 | 8.0 | 8.0 | 7.9 |
| | Lactobacillus | 5.6 | 5.8 | 5.9 | 5.9 | 5.8 | 5.8 |
| | Streptococcus | 6.6 | 6.4 | 6.4 | 6.2 | 6.1 | 6.2 |
| | Staphylococcus | 4.4 | 4.2 | 4.0 | 3.8 | 3.7 | 3.8 |

Means for 10 animals. No of cells per 1 g of feces was expressed in logarithmic value.

As shown in Tables 13 to 17, the group which received milk formulation containing one of the sialic acid derivatives showed a lower fecal score, lower cell numbers of *Clostridium perfringens* and *Escherichia Coli*, and higher cell numbers of Bifidobacteria and Lactobacilli than the group which received milk formulation containing no sialic acid derivatives. From these findings, it was revealed that the sialic acid derivatives have an excellent therapeutic effect on non-infectious diarrhea. From the results of fecal score, each of the sialic acid derivatives showed a markedly higher therapeutic effect than N-acetylneuraminic acid.

INDUSTRIAL APPLICABILITY

The pharmaceutical composition of the present invention can be used as an antiviral agent, an antidiarrheal agent, an antiulcer agent, an anti-inflammatory agent, an anti-allergic agent, and an agent for promoting proliferation of Bifidobacteria. The production method of the present invention makes it possible to produce sialic acid derivatives economically and easily on an industrial scale.

We claim:

1. A pharmaceutical composition characterized by containing as an active ingredient a sialic acid derivative represented by the general formula (1) or (2) below:

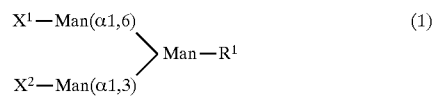
(1)

wherein $R^1$ represents a glycopeptide residue; and $X^1$ and $X^2$, which may be identical or different, represent NeuAc($\alpha$2,6)Gal($\beta$1,4)GlcNAc($\beta$1,2)-, Gal($\beta$1,4)GlcNAc($\beta$1,2)-, or GlcNAc($\beta$1,2)-, provided that at least one of $X^1$ and $X^2$ represents NeuAc($\alpha$2,6)Gal($\beta$1,4)Glc NAc($\beta$1,2)-;

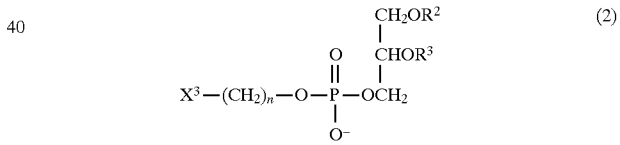
(2)

wherein $R^2$ and $R^3$, which may be identical or different, represent a hydrogen atom or a linear, branched or cyclic, saturated or unsaturated acyl group having 1 to 30 carbon atoms; n is an integer of 1 to 20; and $X^3$ represents a sialic acid derivative residue or a sialyloligosaccharide derivative residue represented by the general formula (3) below:

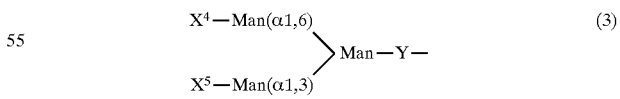
(3)

wherein $X^4$ and $X^5$, which may be identical or different, represent NeuAc($\alpha$2,6)Gal($\beta$1,4)GlcNAc($\beta$1,2)-, Gal($\beta$1,4) GlcNAc($\beta$1,2)- or GlcNAc($\beta$1,2)-, provided that at least one of $X^4$ and $X^5$ represents NeuAc($\alpha$2,6)Gal($\beta$1,4)Glc NAc($\beta$1, 2)-; and Y represents a sugar residue.

2. A method for producing a sialic acid derivative represented by the following general formula (4)

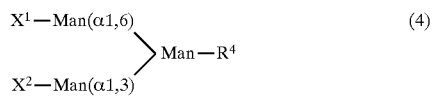

wherein R⁴ represents a sugar residue; $X^1$ and $X^2$, which may be identical or different, represent NeuAc(α2,6)Gal(β1,4)GlcNAc(β1,2)-, Gal(β1,4)GlcNAc(β1,2)- or GlcNAc(β1,2)-, provided that at least one of $X^1$ and $X^2$ represents NeuAc(α2,6)Gal(β1,4)GlcNAc(β1,2)- comprising the steps of:

(a) adding water or brine selected from a potassium salt, a sodium salt and a salt capable of buffering over the range of pH 5 to 10 to avian egg yolk, (b) stirring and filtering the mixture obtained in step (a), (c) adding almond or apricot seed to the filtrate obtained in step (b), (d) stirring the mixture obtained in step (c), (e) subjecting the mixture obtained in step (d) to an anion exchange resin and carrying out elution, and (f) desalting the eluate obtained in step (e).

3. The method according to claim 2, wherein the almond is delipidated.

4. The method according to claim 2, wherein the apricot seed is delipidated.

5. The method according to claim 2, wherein said avian egg yolk is delipidated.

6. The method according to claim 2, wherein the stirring in step (b) is carried out at 40° to 80° C.

7. The method according to claim 2, wherein the stirring in step (d) is carried out at pH 5.0 to 5.5 and 30° to 45° C.

8. The method according to claim 2, wherein the elution in step (e) is carried out using an NaCl solution or a sodium acetate solution.

9. A method of treating illness in a patient comprising administering an effective amount of the pharmaceutical composition of claim 1 to a patient in need thereof, wherein said illness is diarrhea, allergy or inflammation.

10. The method according to claim 9, wherein said illness is caused by a microorganism.

11. The method according to claim 10, wherein said illness is caused by a virus.

12. The method according to claim 11, wherein said illness is diarrhea.

13. The method according to claim 10, wherein said illness is caused by a bacteria.

14. The method according to claim 13, wherein said illness is diarrhea.

15. A method of treating illness in a patient comprising administering an effective amount of the pharmaceutical composition of claim 1 to a patient in need thereof, wherein said pharmaceutical composition promotes the proliferation of Bifidobacteria.

16. The method according to claim 9, wherein said illness is allergy.

17. The method according to claim 9, wherein said illness is inflammation.

18. The method according to claim 9, wherein the effective amount is 0.001 to 1000 mg per kg body weight.

19. The method according to claim 10, wherein the effective amount is 0.001 to 10 mg per kg body weight.

20. The method according to claim 11, wherein the effective amount is 0.001 to 0.3 mg per kg body weight.

21. The method according to claim 9, wherein the illness is diarrhea and the effective amount is 0.5 to 10 mg per kg body weight.

22. The method according to claim 13, wherein the effective amount is 0.001 to 2 mg per kg body weight.

23. A method of treating an ulcer caused by in a patient comprising administering an effective amount of the pharmaceutical composition of claim 1 to a patient in need thereof.

24. The method according to claim 23, wherein the effective amount is 0.001 to 2 mg per kg body weight.

25. The method according to claim 16, wherein the effective amount is 100 to 1000 mg per kg body weight.

26. The method according to claim 9, wherein the illness is allergy and the effective amount is 0.001 to 0.3 mg per kg body weight.

27. The method according to claim 9, wherein the illness is inflammation and the effective amount is 0.001 to 0.1 mg per kg body weight.

* * * * *